(12) United States Patent
Ferrante et al.

(10) Patent No.: US 11,642,501 B2
(45) Date of Patent: May 9, 2023

(54) ROBUST, IMPLANTABLE GAS DELIVERY DEVICE AND METHODS, SYSTEMS AND DEVICES INCLUDING SAME

(71) Applicant: Giner, Inc., Newton, MA (US)

(72) Inventors: Anthony A. Ferrante, Belmont, MA (US); Simon G. Stone, Arlington, MA (US)

(73) Assignee: GINER, INC., Newton, MA (US)

( * ) Notice: Subject to any disclaimer, the term of this patent is extended or adjusted under 35 U.S.C. 154(b) by 829 days.

(21) Appl. No.: 15/971,658

(22) Filed: May 4, 2018

(65) Prior Publication Data

US 2018/0318566 A1 Nov. 8, 2018

Related U.S. Application Data

(60) Provisional application No. 62/501,488, filed on May 4, 2017.

(51) Int. Cl.
*A61M 31/00* (2006.01)
*C25B 1/04* (2021.01)
(Continued)

(52) U.S. Cl.
CPC ...... *A61M 31/002* (2013.01); *A61M 5/14276* (2013.01); *C25B 1/04* (2013.01);
(Continued)

(58) Field of Classification Search
CPC ........ A61M 5/14276; A61M 2005/006; A61M 31/002; A61M 2205/0208;
(Continued)

(56) References Cited

U.S. PATENT DOCUMENTS

| 3,783,868 A | 1/1974 | Bokros |
| 4,853,223 A | 8/1989 | Graf et al. |

(Continued)

FOREIGN PATENT DOCUMENTS

| CN | 105163688 A | 12/2015 |
| CN | 106470731 A | 3/2017 |

(Continued)

OTHER PUBLICATIONS

Liu et al., "Hydrogen therapy: from mechanism to cerebral diseases," Med Gas Res, 6(1):48-54 (2016).

(Continued)

*Primary Examiner* — Katherine H Schwiker
*Assistant Examiner* — Robert F Allen
(74) *Attorney, Agent, or Firm* — Kriegsman & Kriegsman

(57) ABSTRACT

Implantable gas delivery device and methods, systems, and devices including same. According to one embodiment, the implantable gas delivery device includes a porous core that permits facile transport of gas throughout its open volume. The porous core has sufficiently high tensile strength to withstand pressurization without significant deformation. The porous core is generally planar and is shaped to include a pair of opposing surfaces and a periphery. Diffusion membranes are fixed to the two opposing surfaces of the porous core. A gas supply tube has one end inserted into the porous core and another end connectable to a gas source. The periphery of the porous core is sealed gas-tight, either with a gasket or by sealing the porous core and/or diffusion membranes. The device may be used to deliver a gas to an implanted cell capsule or to native cells or tissues or may be used to expel waste gas.

39 Claims, 20 Drawing Sheets

(51) Int. Cl.
  *A61M 5/142* (2006.01)
  *C25B 9/17* (2021.01)
(52) U.S. Cl.
  CPC ........ *C25B 9/17* (2021.01); *A61M 2202/0208* (2013.01); *A61M 2202/09* (2013.01); *A61M 2205/04* (2013.01)
(58) Field of Classification Search
  CPC ...... A61M 2205/04; A61M 13/00–006; A61M 31/00; A61M 2202/0208; A61M 2202/09; Y02E 60/36; C25B 1/04; C25B 9/06; C25B 9/17
  See application file for complete search history.

(56) References Cited

U.S. PATENT DOCUMENTS

| | | | |
|---|---|---|---|
| 5,713,888 A * | 2/1998 | Neuenfeldt | A61F 2/022 604/890.1 |
| 5,951,538 A | 9/1999 | Joshi et al. | |
| 6,368,592 B1 | 4/2002 | Colton et al. | |
| 6,455,518 B2 | 9/2002 | Zenke et al. | |
| 6,686,197 B2 | 2/2004 | Pipeleers | |
| 6,824,915 B1 | 11/2004 | Pedicini | |
| 8,043,271 B2 | 10/2011 | Stern et al. | |
| 8,083,821 B2 | 12/2011 | Tempelman et al. | |
| 8,088,969 B2 | 1/2012 | Elliott et al. | |
| 8,298,813 B2 | 10/2012 | Holman et al. | |
| 8,435,520 B2 | 5/2013 | Schuurman et al. | |
| 8,444,630 B2 | 5/2013 | Rotem et al. | |
| 9,357,764 B2 | 6/2016 | Tempelman et al. | |
| 9,433,557 B2 | 9/2016 | Green et al. | |
| 10,266,808 B2 | 4/2019 | Kelly et al. | |
| 10,272,179 B2 | 4/2019 | Martinson et al. | |
| 10,278,372 B2 | 5/2019 | Hering et al. | |
| 2003/0031652 A1 | 2/2003 | Hering et al. | |
| 2003/0087427 A1* | 5/2003 | Colton | C12M 23/12 435/289.1 |
| 2003/0099622 A1 | 5/2003 | Hering et al. | |
| 2003/0170239 A1 | 9/2003 | Hering et al. | |
| 2004/0213768 A1 | 10/2004 | Elliott et al. | |
| 2005/0074657 A1 | 4/2005 | Rusta-Sallehy et al. | |
| 2005/0136092 A1 | 6/2005 | Rotem et al. | |
| 2005/0267325 A1* | 12/2005 | Bouchier | A61B 17/06004 623/23.72 |
| 2008/0119909 A1 | 5/2008 | Skinner et al. | |
| 2009/0012502 A1 | 1/2009 | Rotem et al. | |
| 2009/0042072 A1 | 2/2009 | Vu et al. | |
| 2010/0108534 A1 | 5/2010 | Carlstrom, Jr. et al. | |
| 2010/0130916 A1 | 5/2010 | Stern et al. | |
| 2010/0196439 A1 | 8/2010 | Beck et al. | |
| 2010/0330547 A1 | 12/2010 | Tempelman et al. | |
| 2011/0008886 A1 | 1/2011 | Hering et al. | |
| 2011/0054387 A1* | 3/2011 | Stern | A61M 39/0208 604/23 |
| 2011/0226686 A1* | 9/2011 | Maurer | B01D 63/02 210/206 |
| 2011/0282444 A1* | 11/2011 | Liu | A61L 27/18 521/154 |
| 2013/0040223 A1 | 2/2013 | Tsukamoto et al. | |
| 2014/0017304 A1 | 1/2014 | Bosmans et al. | |
| 2014/0187574 A1 | 7/2014 | Schuler et al. | |
| 2014/0257515 A1* | 9/2014 | So | A61M 31/002 623/23.64 |
| 2014/0343500 A1* | 11/2014 | Fielder | A61B 17/1739 604/288.01 |
| 2015/0112247 A1* | 4/2015 | Tempelman | A61F 2/022 435/283.1 |
| 2015/0164990 A1 | 6/2015 | Geaney et al. | |
| 2016/0228377 A1 | 8/2016 | Bomans et al. | |
| 2016/0274087 A1 | 9/2016 | Assefa et al. | |
| 2016/0361365 A1 | 12/2016 | Lee et al. | |
| 2018/0125632 A1* | 5/2018 | Cully | A61M 5/00 |
| 2018/0133383 A1* | 5/2018 | Ferrante | A61F 2/022 |
| 2018/0135948 A1 | 5/2018 | Stone et al. | |
| 2018/0340146 A1 | 11/2018 | Ferber | |
| 2019/0119462 A1 | 4/2019 | Desai et al. | |
| 2019/0125668 A1 | 5/2019 | Fox et al. | |
| 2019/0125937 A1 | 5/2019 | Rotem et al. | |
| 2019/0134097 A1 | 5/2019 | Ferber | |
| 2019/0343615 A1 | 11/2019 | Dalton et al. | |

FOREIGN PATENT DOCUMENTS

| | | |
|---|---|---|
| EP | 2964147 B1 | 5/2018 |
| JP | 2013519411 A | 5/2013 |
| JP | 2013528067 A | 7/2013 |
| JP | 2016512022 A | 4/2016 |
| JP | 2016530980 A | 10/2016 |
| WO | 9319700 A1 | 10/1993 |
| WO | 9404169 A1 | 3/1994 |
| WO | 9742953 A1 | 11/1997 |
| WO | 0150983 A1 | 7/2001 |
| WO | 2006122169 A2 | 11/2006 |
| WO | 2008079997 A2 | 7/2008 |
| WO | 2009031154 A2 | 3/2009 |
| WO | 2011143219 A1 | 11/2011 |
| WO | 2014138691 A1 | 9/2014 |
| WO | 2014171842 A1 | 10/2014 |
| WO | 2015048184 A1 | 4/2015 |
| WO | 2015145264 A2 | 10/2015 |
| WO | 2017218714 A1 | 12/2017 |
| WO | 2018085714 A1 | 5/2018 |
| WO | 2018093956 A1 | 5/2018 |
| WO | 2018102077 A2 | 6/2018 |
| WO | 2018144098 A1 | 8/2018 |
| WO | 2018144099 A1 | 8/2018 |
| WO | 2018204867 A1 | 11/2018 |
| WO | 2018207179 A1 | 11/2018 |
| WO | 2018220621 A2 | 12/2018 |
| WO | 2018220622 A2 | 12/2018 |
| WO | 2018220623 A1 | 12/2018 |
| WO | 2019067766 A1 | 4/2019 |
| WO | 2019089943 A1 | 5/2019 |
| WO | 2019089993 A1 | 5/2019 |
| WO | 2019241562 A1 | 12/2019 |

OTHER PUBLICATIONS

Chen et al., "Hydrogen Gas Reduced Acute Hyperglycemia-Enhanced Hemorrhagic Transformation in a Focal Ischemia Rat Model," Neuroscience, 169:402-414 (2010).
Ishibashi et al., "Consumption of water containing a high concentration of molecular hydrogen reduces oxidative stress and disease activity in patients with rheumatoid arthritis: an open-label pilot study," Med Gas Res, 2:27-34 (2012).
Ishibashi et al., "Improvement of psoriasis-associated arthritis and skin lesions by treatment with molecular hydrogen: a report of three cases." Molecular Medicine Reports, 12:2757-2764 (2015).
Tamura et al., "Feasibility and Safety of Hydrogen Gas Inhalation for Post-Cardiac Arrest Syndrome," Circulation Journal, 80:1870-1873 (2016).
Chi et al., "Electrochemical Generation of Free Nitric Oxide from Nitrite Catalyzed by Iron meso-Tetrakis(4-N-methylpyridiniumyl)porphyrin," Inorg. Chem., 43:8437-8446 (2004).
Ren et al., "Electrochemically Modulated Nitric Oxide (NO) Releasing Biomedical Devices via Copper(II)-Tri(2-pyridylmethyl)amine Mediated Reduction of Nitrite," ACS Appl. Mater. Interfaces, 6:3779-3783 (2014).
Avgoustiniatos et al., "Engineering Challenges in Immunoisolation Device Development," Principles of Tissue Engineering, pp. 594-613 (2000).
Ono et al., "A basic study on molecular hydrogen (H2) inhalation in acute cerebral ischemia patients for safety check with physiological parameters and measurement of blood H2 level," Med Gas Res, 2:21-27 (2012).
Bilal et al., "Thermo-electrochemical reduction of sulfate to sulfide using a graphite cathode," Journal of Applied Electrochemistry, 28: 1073-1081 (1998).

(56) References Cited

OTHER PUBLICATIONS

International Search Report dated Jul. 23, 2018, from PCT/US18/31223, the corresponding PCT application to the present application.
Written Opinion dated Jul. 23, 2018, from PCT/US18/31223, the corresponding PCT application to the present application.
Wang et al., "Donor Treatment With Carbon Monoxide Can Yield Islet Allograft Survival and Tolerance," Diabetes, 54:1400-6 (2005).
Avgoustiniatos et al., "Effect of External Oxygen Mass Transfer Resistances on Viability of Immunoisolated Tissue," Ann N Y Acad Sci, 831:145-67 (1997).
Luo et al., "Recovery of Neurological Functions in Non-Human Primate Model of Parkinson's Disease by Transplantation of Encapsulated Neonatal Porcine Choroid Plexus Cells," J Parkinsons Dis, 3:275-91 (2013).
Tarantal et al., "Real-time Bioluminescence Imaging of Macroencapsulated Fibroblasts Reveals Allograft Protection in Rhesus Monkeys (*Macaca mulatta*)," Transplantation, 88(1):38-41 (2009).
Tibell et al., "Survival of Macroencapsulated Allogenic Parathyroid Tissue One Year After Transplantation in Nonimmunosuppressed Humans," Cell Transplantation, 10:591-9 (2001).
O'Sullivan et al., "Islets Transplanted in Immunoisolation Devices: a Review of the Progress and the Challenges that Remain," Endocrine Reviews, 32(6):827-44 (2011).
Gore Technologies, retrieved from <URL:https://web.archive.org/web/20161112003850/https:/fwww.gore/com/about/technologies> (Nov. 12, 2016).

\* cited by examiner

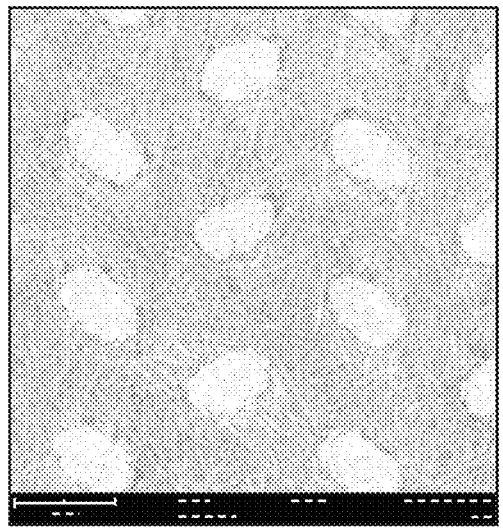 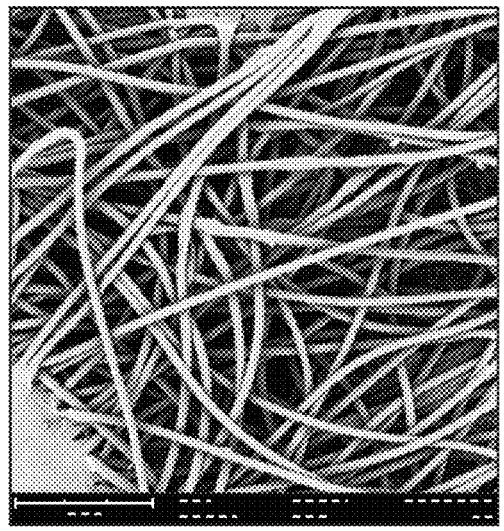
FIG. 18A　　　　　　　　　　　FIG. 18B
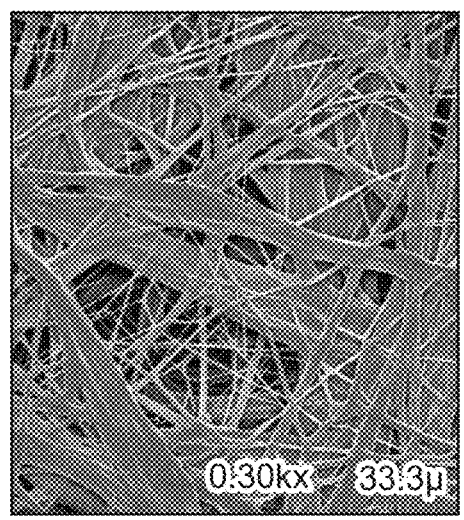
FIG. 19

ROBUST, IMPLANTABLE GAS DELIVERY DEVICE AND METHODS, SYSTEMS AND DEVICES INCLUDING SAME

CROSS-REFERENCE TO RELATED APPLICATIONS

The present application claims the benefit under 35 U.S.C. 119(e) of U.S. Provisional Patent Application No. 62/501,488, inventors Anthony A. Ferrante et al., filed May 4, 2017, the disclosure of which is incorporated herein by reference.

FEDERALLY SPONSORED RESEARCH OR DEVELOPMENT

This invention was made with government support under R44 DK100999 awarded by National Institutes of Health. The government has certain rights in the invention.

BACKGROUND OF THE INVENTION

The present invention relates generally to implantable medical devices useful in the treatment of diseases, disorders, and/or conditions and relates more particularly to such devices that may be used in the delivery of one or more gases.

Implantable medical devices (or "implant devices") are commonly-employed tools that may be used, for example, to provide therapeutics in the treatment of various diseases, disorders, and/or conditions. Examples of treatments involving implant devices include the controlled delivery of therapeutic gases, the controlled delivery of pharmaceutical products, and the delivery of therapeutic cells and/or tissues. A variety of implant devices have been developed to control the delivery of such therapeutics. In cases where therapeutic cells and/or tissues are implanted, such implant devices typically rely on a large form factor or structural member with low cell density to supply gases and nutrients by diffusion.

Recently, the use of therapeutic gases to treat human diseases and injuries has received increasing attention. In particular, molecular hydrogen has been proposed as a therapeutic agent for the treatment of a broad range of indications including stroke, traumatic brain injury, Parkinson's disease, rheumatoid arthritis, psoriasis, and diabetes, and as a neuroprotective agent after ischemia induced by cardiac arrest (see Liu et al., "Hydrogen Therapy: From Mechanism to Cerebral Diseases," *Med Gas Res*, 6:48-54 (2016), which is incorporated herein by reference). Molecular hydrogen has been found to have anti-inflammatory effects in animal models and in humans, and is known to neutralize reactive oxygen species that are elevated in patients experiencing oxidative stress. Techniques for delivering molecular hydrogen have included inhalation, infusion with hydrogen-infused saline, and consumption of water that is saturated with hydrogen gas at atmospheric or greater pressure.

Some of the advantages of molecular hydrogen therapy include a lack of toxicity. In addition, animal studies have shown strong protection in ischemic stroke (see Chen et al., "Hydrogen Gas Reduced Acute Hyperglycemia-Enhanced Hemorrhagic Transformation in a Focal Ischemia Rat Model," *Neuroscience*, 169:402-414 (2010), which is incorporated herein by reference). Recent clinical studies have demonstrated significant therapeutic effects in humans. In one such study, 20 rheumatoid arthritis patients were treated with hydrogen-saturated water daily for four weeks (see Ishibashi et al., *Med Gas Res*, "Consumption of Water Containing a High Concentration of Molecular Hydrogen Reduces Oxidative Stress and Disease Activity in Patients with Rheumatoid Arthritis: An Open-Label Pilot Study," 2:27 (2012), which is incorporated herein by reference). Markers of oxidative stress were reduced, as was the mean DAS28 score (disease activity score for 28 joints). In another study, three patients were treated with molecular hydrogen using several delivery modalities (see Ishibashi et al., "Improvement of Psoriasis-Associated Arthritis and Skin Lesions by Treatment with Molecular Hydrogen: A Report of Three Cases," *Mol Med Rep*, 12:2757-64 (2015), which is incorporated herein by reference). Inflammatory cytokine levels were reduced, as were the DAS28 and PASI (psoriasis-associated inflammation) scores. In yet another study, five patients who had undergone cardiac arrest were treated with molecular hydrogen for 18 hours via inhalation to determine if treatment could protect against neurological injury due to anoxia during cardiac arrest (see Tamura et al., "Feasibility and Safety of Hydrogen Gas Inhalation for Post-Cardiac Arrest Syndrome—First-in-Human Pilot Study," *Circ J*, 80:1870-3 (2016), which is incorporated herein by reference). The four surviving patients had 90-day CPC (cerebral performance category) scores of 1. This includes a patient who had high NSE (neuron-specific enolase), which is a strong predictor of poor neurologic outcome.

Despite the promise of molecular hydrogen therapy, its adoption has been slow. Delivery by inhalation or infusion is cumbersome for patients who are ambulatory or for chronic use. Consumption of hydrogen-saturated beverages is limited by the low solubility of gaseous hydrogen in water, and by variability in uptake between patients.

In addition to gaseous hydrogen, other gases have been used for cell therapies. While oxygen is known to be needed for cellular viability and function, there are other gases that can be delivered to a cellular implant, or to the vicinity of such an implant, and that can provide benefits to implanted cells and/or surrounding tissue. For example, gaseous carbon dioxide may be useful in regulating metabolism, and gaseous carbon monoxide may have anti-inflammatory and antiapoptotic effects (see Wang et al., "Donor Treatment with Carbon Monoxide Can Yield Islet Allograft Survival and Tolerance," *Diabetes*, 54:1400-6 (2005), which is incorporated herein by reference). Carbon monoxide may be generated electrochemically. Similarly to carbon monoxide, nitric oxide and hydrogen sulfide are gases that can be generated electrochemically (see Chi et al., "Electrochemical Generation of Free Nitric Oxide from Nitrite Catalyzed by Iron Meso-Tetrakis(4-N-Methylpyridiniumyl) porphyrin," *Inorg Chem*, 43:8437-8446 (2004); Ren et al., "Electrochemically Modulated Nitric Oxide (NO) Releasing Biomedical Devices via Copper(II)-Tri(2-pyridylmethyl)amine Mediated Reduction of Nitrite," *ACS Appl Mater Interfaces*, 6:3779-3783 (2014); Bilal et al., "Thermo-Electrochemical Reduction of Sulfate to Sulfide Using a Graphite Cathode," *Journal of applied electrochemistry*, 28:1073-81 (1998), all of which are incorporated herein by reference) and are implicated in several key cell signaling pathways. As such, these gases may be applied beneficially in tissue therapy applications where protection against hypoxia, toxic reactive oxygen species, and inflammation in endothelial structures, for instance, are desired.

As noted above, in addition to being used to deliver therapeutic gases, implant devices have also been used to deliver therapeutic cells and/or tissues. In fact, there is a long history of research into cellular therapies, specifically encapsulated cellular implants. Encapsulation generally falls into two categories: microencapsulation and macroencapsulation. In microencapsulation, implanted cells or tissues are placed in a matrix (e.g., hydrogel), with a relatively small quantity of cells in the matrix. The matrix may or may not provide immunoprotection to the implanted cells within the matrix. Such microcapsules are generally placed in the peritoneal cavity of a patient and are not readily retrievable. In macroencapsulation, there is generally a porous membrane surrounding (i.e., encapsulating) the implanted cells; a matrix surrounding the cells may or may not be included. The macroencapsulation membrane may perform one or more functions, including keeping the implanted cells contained, isolating the implanted cells from the host immune system, helping the implant to integrate into the body (i.e., vascularize), and facilitating the implant from becoming fully walled-off from the body by fibrosis. Macrocapsules are generally designed to be retrieved from the body for both safety and replacement. Generally, a single macrocapsule or a plurality of macrocapsules may be used to effect treatment.

Macroencapsulated implants generally include a thin form factor or structural member, which is typically in the form of a planar sheet or a thin, tall cylinder, in acknowledgement of the fact that, in normal physiology, cells are typically located within several hundred micrometers of a blood vessel supplying nutrients to such cells by diffusion. However, even the thinnest dimensions typically have been larger than the optimal physiological distance, and the majority of implants have had necrotic cell cores of varying dimensions, as seen by histological examination. These necrotic cores are the result of cellular death in the central region. The limiting nutrient based on reaction diffusion models is generally considered to be oxygen (see Avgoustiniatos et al., "*Design Considerations in Immunoisolation,*" *Principles of tissue engineering*, RG Landes Co., Austin, Tex. p. 336-346 (1997); Avgoustiniatos et al., "Effect of External Oxygen Mass Transfer Resistances on Viability of Immunoisolated Tissue," *Ann N Y Acad Sci*, 831:145-67 (1997), both of which are incorporated herein by reference) because of oxygen's low availability compared to other nutrients, such as glucose. The necrotic cores have been more extensive (i.e., larger in dimension) when the cellular density is high, further increasing oxygen demand. In general, high cellular density is necessary for cellular implants to have a desired therapeutic effect while remaining sufficiently compact in size to be practical for surgical implant and for available implant sizes.

Cellular implants have been most extensively proposed for creating a bio-artificial pancreas, typically with islets or other insulin-secreting and/or glucose-regulating cells. However, cellular implants have also been proposed and researched for the treatment of liver failure, Parkinson's disease (see Luo et al., "Recovery of Neurological Functions in Non-Human Primate Model of Parkinson's Disease by Transplantation of Encapsulated Neonatal Porcine Choroid Plexus Cells," *J Parkinsons Dis*, 3:275-91 (2013), which is incorporated herein by reference), (para)thyroid disease, hemophilia, Alzheimer's, and pain control, as well as other conditions and diseases. Implants that secrete insulin, human growth hormone, dopamine, catecholamine, and other physiological active and/or therapeutic compounds have been attempted.

Cell implant macro-scale devices have been designed, fabricated, and tested for use with islets and other cell types. Some have been successfully tested in small and large animal models (see Tarantal et al., "Real-Time Bioluminescence Imaging of Macroencapsulated Fibroblasts Reveals Allograft Protection in Rhesus Monkeys (Macaca Mulatta)," *Transplantation*, 88:38-41 (2009), which is incorporated herein by reference) and, to a limited extent, in humans with excellent biocompatibility and safety profiles (see Tibell et al., "Survival of Macroencapsulated Allogeneic Parathyroid Tissue One Year after Transplantation in Nonimmunosuppressed Humans," *Cell Transplant*, 10:591-9 (2001), which is incorporated herein by reference). Such devices have also demonstrated protection from allo- and auto-immunity with no immunosuppression in non-human primates with one study in human subjects and with xeno-immunity with low immunosuppression. However, work with large-animal models and islet sources more relevant to clinical application showing therapeutic efficacy is lacking.

To date, the scale-up of cell therapy devices for human use has been severely impaired by the device size requirements necessary for sufficient islet oxygenation to support islet viability and function (see O'Sullivan et al., "Islets transplanted in immunoisolation devices: a review of the progress and the challenges that remain," *Endocr Rev*, 32(6):827-44 (2011), which is incorporated herein by reference). Islets (especially islet (3-cells) are particularly sensitive to hypoxia. In addition to its effect on islet viability, oxygen deprivation has a dramatic effect on islet function, as measured by glucose-stimulated insulin secretion (GSIS). GSIS is an energy-dependent process and the threshold for oxygen effects is seen at oxygen levels 100-fold higher than those needed to affect viability.

Various patent-related documents disclose cell implant devices. For example, in U.S. Patent Application Publication No. US 2015/0112247 A1, inventors Tempelman et al., which was published Apr. 23, 2015, and which is incorporated by reference, there is disclosed a system for gas treatment of a cell implant. According to one embodiment of the aforementioned publication, the system includes (i) an electrochemical device configured to output a first gas, (ii) a cell containment subsystem comprising a first chamber configured to receive cells, and (iii) a gas conduit for conveying the first gas from the electrochemical device to the first chamber, the gas conduit being coupled at one end to the electrochemical device and at an opposite end to the first chamber. According to another embodiment, the cell containment subsystem includes both a gas chamber and cell chambers on one or both sides of the gas chamber. In the aforementioned embodiment, the gas chamber receives the first gas from the electrochemical device, and the first gas is then delivered from the gas chamber to the one or more cell chambers.

The present inventors have discovered, however, that, with the above-described system, the gas that is delivered to the cell containment subsystem is under significant pressure. In fact, the gas pressure is sufficiently great as to cause the cell containment subsystem to swell and to be at a significant risk for rupture at the pressures likely required for effective therapy.

Other patent-related documents that may be of interest include the following, all of which are incorporated herein by reference: U.S. Pat. No. 8,444,630 B2, inventors Rotem et al., issued May 21, 2013; U.S. Pat. No. 6,368,592, inventors Colton et al., issued Apr. 9, 2002; U.S. Patent Application Publication No. US 2011/0054387 A1, inventors Stern et al., published Mar. 3, 2011; U.S. Patent Application Publication No. 2010/0330547 A1, inventors Tempelman et al., published Dec. 30, 2010; U.S. Patent Application Publication No. US 2009/0012502 A1, inventors Rotem et al., published Jan. 8, 2009; US 2005/0136092

A1, inventors Rotem et al., published Jun. 23, 2005; U.S. Patent Application Publication No. US 2003/0087427 A1, inventors Colton et al., published May 8, 2003; PCT International Publication No. WO 2009/031154 A2, published Mar. 12, 2009; PCT International Publication No. WO 2008/079997 A2, published Jul. 3, 2008; PCT International Publication No. WO 2006/122169 A2, published Nov. 16, 2006; and PCT International Publication No. WO 01/50983 A1, published Jul. 19, 2001.

SUMMARY OF THE INVENTION

According to one aspect of the invention, there is provided an implantable gas delivery device, the implantable gas delivery device comprising (a) a porous core, the porous core having an open volume and permitting transport of gas throughout the open volume, the porous core having a tensile strength in all directions sufficient to withstand a tensile stress without permanent deformation; (b) at least one gas-permeable diffusion membrane, the at least one gas-permeable diffusion membrane being fixedly coupled to a surface of the porous core, whereby deformation and/or delamination of the at least one gas-permeable diffusion membrane is limited by attachment of the at least one diffusion membrane to the porous core; (c) a gas supply tube, the gas supply tube having a first end inserted into the porous core and having a second end adapted to receive gas from a gas source; (d) wherein any surfaces of the porous core unoccupied by the at least one gas-permeable diffusion membrane and the gas supply tube are sealed gas-tight; and (e) wherein the implantable gas delivery device has a planar geometry and a gas-tight seal and, when pressurized, maintains the planar geometry and the gas-tight seal.

In a more detailed feature of the invention, the porous core may comprise a biocompatible material selected from the group consisting of one or more of sintered polymers, woven and non-woven polymers, rigid open cell foams, porous ceramics, porous metals, and combinations thereof.

In a more detailed feature of the invention, the porous core may comprise a sintered polymer selected from the group consisting of sintered polyethylene, sintered polypropylene, sintered polyethylene terephthalate, sintered polyvinylidene fluoride, sintered polytetrafluoroethylene, and combinations thereof.

In a more detailed feature of the invention, the porous core may comprise a woven or non-woven polymer mesh, and the woven or non-woven polymer mesh may comprise a material selected from the group consisting of polyethylene terephthalate, polyethylene, polypropylene, polyamide, polyvinylidene fluoride, and combinations thereof.

In a more detailed feature of the invention, the porous core may be a monolithic structure made of a single layer.

In a more detailed feature of the invention, the porous core may be a composite structure made of a plurality of layers and/or a plurality of materials.

In a more detailed feature of the invention, the porous core may be formed by fusing together two layers.

In a more detailed feature of the invention, the at least one gas-permeable diffusion membrane may comprise a porous membrane.

In a more detailed feature of the invention, the porous membrane may comprise a hydrophilic microporous membrane.

In a more detailed feature of the invention, the hydrophilic microporous membrane may be selected from the group consisting of microporous hydrophilized expanded polytetrafluoroethylene membranes, microporous hydrophilic polyvinylidene fluoride membranes, microporous polyethersulfone membranes, hydrophilized microporous polyethylene terephthalate track etch membranes, microporous hydrophilic polyethylene membranes, and combinations thereof.

In a more detailed feature of the invention, the at least one gas-permeable diffusion membrane may comprise a non-porous, gas-permeable material.

In a more detailed feature of the invention, the non-porous, gas-permeable material may comprise a silicone layer.

In a more detailed feature of the invention, the at least one gas-permeable diffusion membrane may be a monolithic structure made of a single layer.

In a more detailed feature of the invention, the at least one gas-permeable diffusion membrane may be a laminate structure comprising a plurality of layers.

In a more detailed feature of the invention, the at least one gas-permeable diffusion membrane may be a laminate structure comprising a hydrophilic microporous membrane and a hydrophobic membrane, the hydrophobic membrane may face towards the porous core, and the hydrophilic membrane may face away from the porous core.

In a more detailed feature of the invention, the at least one gas-permeable diffusion membrane may be a laminate structure comprising a hydrophilic microporous membrane and a vascularizing membrane, the hydrophilic microporous membrane may face towards the porous core, and the vascularizing membrane may face away from the porous core.

In a more detailed feature of the invention, the at least one gas-permeable diffusion membrane may be directly bonded to the porous core.

In a more detailed feature of the invention, the at least one gas-permeable diffusion membrane may be indirectly bonded to the porous core.

In a more detailed feature of the invention, the porous core may be shaped to comprise two opposing surfaces and a periphery, and the periphery may extend between the two opposing surfaces.

In a more detailed feature of the invention, the at least one gas-permeable diffusion membrane may comprise a first gas-permeable diffusion membrane and a second gas-permeable diffusion membrane, the first gas-permeable diffusion membrane may be fixedly coupled to one of the two opposing surfaces of the porous core, and the second gas-permeable diffusion membrane may be fixedly coupled to the other of the two opposing surfaces of the porous core.

In a more detailed feature of the invention, the porous core may be sealed gas-tight by an integral edge-seal of the porous core.

In a more detailed feature of the invention, the at least one gas-permeable diffusion membrane may comprise two gas-permeable diffusion membranes, and the porous core may be sealed gas-tight by edge-sealing together the two gas-permeable diffusion membranes. Alternatively, where the two gas-permeable membranes are porous, the porous core may be compressed and melted around its edges so that the melted porous core flows into the pores of the gas-permeable membranes, wherein the combination of the porous core melting and being compressed, and the porous core flowing into the pores of the gas-permeable membranes forms a seal. Alternatively, the material that forms a porous core and the gas-permeable membranes all may be melted to form a uniform seal.

In a more detailed feature of the invention, the porous core may be sealed gas-tight with a gasket.

In a more detailed feature of the invention, the gasket may be a structural gasket.

In a more detailed feature of the invention, the gasket may be a thermoplastic gasket.

In a more detailed feature of the invention, the gasket may be a thermoset resin.

In a more detailed feature of the invention, the gasket may be an adhesive.

In a more detailed feature of the invention, the implantable gas delivery device may further comprise at least one tissue-integrating layer, the at least one tissue-integrating layer being coupled to the at least one gas-permeable diffusion layer on a side opposite to the porous core.

In a more detailed feature of the invention, the implantable gas delivery device may further comprise at least one hydrophobic layer, and the at least one hydrophobic layer may be interposed between the at least one gas-permeable diffusion membrane and the porous core.

According to another aspect of the invention, there is provided an implant device, the implant device comprising (a) the implantable gas delivery device as described above; and (b) at least one capsule containing implanted cells or tissues, the at least one capsule being in direct contact with the implantable gas delivery device to receive gas therefrom.

In a more detailed feature of the invention, the at least one capsule may comprise a plurality of capsules containing implanted cells or tissues, and each of the plurality of capsules may be in direct contact with the implantable gas delivery device to receive gas therefrom.

According to still another aspect of the invention, there is provided an implant system, the implant system comprising: (a) an implantable gas source, the implantable gas source comprising a first outlet for outputting a first gas; (b) the implantable gas delivery device as described above, wherein the gas supply tube of the implantable gas delivery device is fluidically coupled to the first outlet of the implantable gas source so as to receive the first gas from the implantable gas source.

In a more detailed feature of the invention, the implantable gas source may be a water electrolyzer.

In a more detailed feature of the invention, the implantable gas source may further have a second outlet for outputting a second gas, the implant system may further comprise a percutaneous venting device, and the percutaneous venting device may be fluidically coupled to the second outlet of the implantable gas source so as to receive the second gas from the implantable gas source.

In a more detailed feature of the invention, the first gas received by the implantable gas delivery device may be oxygen, and the second gas received by the percutaneous venting device may be hydrogen.

In a more detailed feature of the invention, the first gas received by the implantable gas delivery device may be hydrogen, and the second gas received by the percutaneous venting device may be oxygen.

According to a further aspect of the invention, there is provided an implant system, the implant system comprising (a) an implantable gas source, the implantable gas source comprising a first outlet for outputting a first gas and a second outlet for outputting a second gas; (b) first and second implantable gas delivery devices, each of the first and second implantable gas delivery devices being identical to the implantable gas delivery device described above, wherein the gas supply tube of the first implantable gas delivery device is fluidically coupled to the first outlet of the implantable gas source so as to receive the first gas from the implantable gas source and wherein the gas supply tube of the second implantable gas delivery device is fluidically coupled to the second outlet of the implantable gas source so as to receive the second gas from the implantable gas source.

In a more detailed feature of the invention, the system may further comprise at least one capsule containing cells and/or tissues, and the at least one capsule may be in direct contact with the first implantable gas delivery device to receive gas therefrom.

According to still a further aspect of the invention, there is provided a method of delivering a therapeutic gas to a patient, the method comprising the steps of (a) providing the implantable gas delivery device as described above; (b) implanting the implantable gas delivery device in an aqueous environment in a patient at a location where the at least one gas-permeable diffusion membrane is sufficiently close to tissue that gas released from the gas-permeable diffusion membrane is taken up by the circulatory system of the patient as a gas dissolved in an aqueous medium; and (c) supplying a therapeutic gas to the implantable gas delivery device, whereby the therapeutic gas is released from the gas-permeable diffusion membrane as gas dissolved in aqueous medium.

In a more detailed feature of the invention, the therapeutic gas may be hydrogen.

According to still yet a further aspect of the invention, there is provided an implant device comprising (a) a central electrolyzer assembly, the central electrolyzer assembly having a first face outputting oxygen and a second face outputting hydrogen; (b) a first porous core fluidically and mechanically coupled to the first face of the central electrolyzer, the first porous core having an open volume and permitting transport of gas throughout the open volume, the first porous core having a tensile strength in all directions sufficient to withstand a tensile stress without permanent deformation; (c) a second porous core fluidically and mechanically coupled to the second face of the central electrolyzer, the second porous core having an open volume and permitting transport of gas throughout the open volume, the second porous core having a tensile strength in all directions sufficient to withstand a tensile stress without permanent deformation; and (d) a cell capsule, the cell capsule including a first gas-permeable diffusion membrane, the first gas-permeable diffusion membrane being fixedly coupled to a surface of the porous core opposite the central electrolyzer, whereby deformation and/or delamination of the at least one gas-permeable diffusion membrane is limited by attachment of the at least one diffusion membrane to the porous core.

For purposes of the present specification and claims, various relational terms like "top," "bottom," "proximal," "distal," "upper," "lower," "front," and "rear" may be used to describe the present invention when said invention is positioned in or viewed from a given orientation. It is to be understood that, by altering the orientation of the invention, certain relational terms may need to be adjusted accordingly.

Additional objects, as well as aspects, features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. These drawings are not necessarily drawn to scale, and certain components may have undersized and/or oversized dimensions for purposes of explication. In the drawings wherein like reference numeral represent like parts:

FIGS. 18A and 18B are a photograph and a scanning electron micrograph, respectively, of a fabric containing layers of spunbond and meltblown polypropylene, said fabric being suitable for use as a porous core of a gas delivery device of the present invention;

FIG. 19 is a scanning electron micrograph of a porous high density polyethylene film fabricated by flash spinning, said film being suitable for use as a porous core of a gas delivery device of the present invention;

DETAILED DESCRIPTION OF THE INVENTION

Figure 1A:
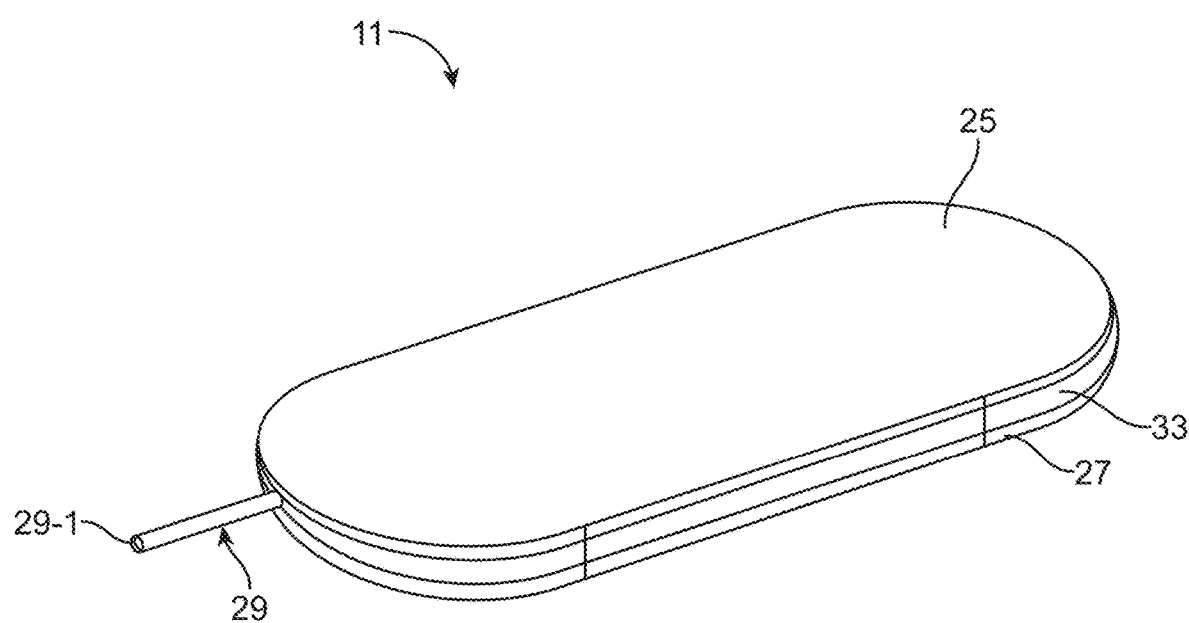
FIGS. 1A and 1B are simplified perspective and exploded perspective views, respectively, of a first embodiment of a gas delivery device constructed according to the present invention.

As discussed above, there are various situations in which it is desirable to deliver a therapeutic gas to the interior of a body. In such situations, it is necessary to have a safe, effective means to deliver the gas in a controlled manner so that the diffusion rate does not exceed the capacity of the receiving environment to absorb the gas. For example, it may be desirable to deliver a therapeutic gas, such as one or more of oxygen, hydrogen, hydrogen sulfide, nitric oxide, carbon monoxide, and carbon dioxide, to tissue that has suffered injury. In such a case, it would be desirable for a delivery device to be implanted near the point of injury so that the therapeutic gas may be delivered across the device surface to deliver a therapeutic dose to the affected area. In another example, it may be desirable to deliver a therapeutic gas systemically using a device with a surface designed to encourage close vascularization. In still another example, it may be desirable to deliver one or more therapeutic gases, such as, but not limited to, oxygen and hydrogen, to an integrated compartment that contains cellular therapeutics, without running the risk that excessive gas pressures may cause damage to the integrated compartment.

The present invention is directed, in part, at a novel implant device that addresses many of the above needs. More specifically, according to one embodiment, the novel implant device comprises a gas delivery device. As will be discussed further below, the gas delivery device of the present invention is preferably configured in such a way that it delivers gas in a controlled manner, for example, by passing the gas through a diffusion membrane that dissolves the gas in water and/or that controls the rate of gas flow therethrough. In this manner, the deleterious effects resulting from delivering a gas at a high gas pressure are significantly reduced.

The gas delivery device of the present invention may be used in many ways to deliver one or more gases to a desired location. For example, the gas delivery device may be used to deliver one or more therapeutic gases to one or more cell capsules implanted within a patient. Alternatively, the gas delivery device may be used to deliver one or more therapeutic gases to a targeted location within a patient where specific cells or tissues are present in their native state. Alternatively, the gas delivery device may be used to deliver one or more therapeutic gases to the circulatory system of the patient for dissemination of the gases throughout the patient, either for a systemic effect or for a more targeted effect on cells or tissues where the gases may have a particular therapeutic impact. Alternatively, the gas delivery device may be used to deliver one or more waste gases to the circulatory system of the patient for expulsion from the patient through the patient's respiratory system. Alternatively, the gas delivery device may be used to deliver one or more waste gases for expulsion to a percutaneous gas diffusion device of the type disclosed in U.S. patent application Ser. No. 15/814,298, inventors Ferrante et al., filed Nov. 15, 2017, which is incorporated herein by reference.

The one or more gases delivered by the gas delivery device of the present invention may be generated in situ within the patient, for example, using an implanted electrochemical gas generating device, examples of which are disclosed in U.S. Patent Application Publication No. US 2015/0112247 A1 and in U.S. patent application Publication Ser. No. 15/814,124, inventors Stone et al., filed Nov. 15, 2017, both of which are incorporated herein by reference. A gas generated in this manner may then be supplied to the gas delivery device using a supply tube coupled at one end to the implanted electrochemical gas generating device and coupled at another end to the gas delivery device. Alternatively, instead of generating a gas in situ within the patient, the one or more gases supplied to the gas delivery device may be generated outside of the patient, either electrochemically or otherwise, and then may be conveyed to the gas delivery device, for example, using a percutaneous gas diffusion device of the type disclosed in U.S. Ser. No. 15/814,298 and/or a supply tube. Alternatively, the one or more gases may be provided, either continuously or periodically, to a gas storage device within the patient and then conveyed from the gas storage device to the gas delivery device using a supply tube or other means.

The implant device of the present invention may further comprise, in addition to the gas delivery device, one or more cell capsules coupled to the gas delivery device. In this manner, for example, the gas delivery device may be used to deliver one or more gases to each of the one or more cell capsules.

The present invention is also directed, in part, at a system for delivering one or more gases to cells or tissues, whether such cells or tissues are implanted or native. According to one embodiment, the system may comprise a gas delivery device as described above and may further comprise a gas generating device. The gas generating device may be an implanted electrochemical gas generating device of the type described above, and the gas delivery device and the gas generating device may be coupled to one another, for example, with a supply tube that may be connected at one end to the gas generating device and at another end to the gas delivery device. According to another embodiment, the system may further comprise one or more cell capsules coupled to the gas delivery device. For example, where the gas generating device is a water electrolyzer, the system may comprise a first gas delivery device that is coupled to the oxygen outlet of the water electrolyzer, and a second gas delivery device that is coupled to the hydrogen outlet of the water electrolyzer. If desired, the first gas delivery device may then be used, for example, to supply the one or more cell capsules with oxygen and the second gas delivery device may be used, for example, to deliver hydrogen to a percutaneous gas diffusion device or to the bloodstream for expulsion from the patient and/or to the bloodstream for dissemination throughout the patient for a therapeutic effect. Alternatively, where no cell capsules are present, the first gas delivery device may be used, for example, to deliver oxygen to a percutaneous gas diffusion device or to the bloodstream for expulsion from the patient, and the second gas delivery device may be used, for example, to deliver hydrogen to the bloodstream for dissemination throughout the patient for a therapeutic effect or directly to a nearby tissue.

Broadly stated, the gas delivery device of the present invention may include (i) a porous core through which gas is permitted to move freely by convection and/or diffusion, the porous core preferably having sufficient tensile strength in all directions sufficient to withstand a tensile stress (for example, pressurization up to about 25 psi, preferably up to about 50 psi), without permanent deformation; and (ii) at least one gas-permeable diffusion membrane (sometimes referred to herein simply as "diffusion membrane") securely fixed (e.g., by bonding) to the porous core.

The porous core may be formed from a variety of biocompatible materials but should allow rapid equilibration of gas therethrough via diffusion and/or convection. The porous core may be a monolithic structure made of a single layer and a single material or may be a composite structure made of a plurality of layers and/or a plurality of materials. Examples of materials suitable for use in the porous core may include one or more of sintered polymers, woven and non-woven polymers, rigid open cell foams, porous ceramics, and porous metals.

Sintered polymers suitable for use in the porous core may include, but are not limited to, sintered biocompatible polymers, such as sintered polyethylene, sintered polypropylene, sintered polyethylene terephthalate, sintered polyvinylidene fluoride, sintered polytetrafluoroethylene, and combinations thereof. An example of such a sintered polymer material may include a sintered, ultra-high molecular weight polyethylene (UBMWPE), such as is commercially available as POREX® XS-96193 sintered material (Porex Filtration Group Inc., Fairburn, Ga.).

Woven and non-woven polymers suitable for use in the porous core may include, but are not limited to, polymer meshes. Such woven and non-woven polymer meshes may comprise a material selected from the group consisting of polyethylene terephthalate, polyethylene, polypropylene, polyamide, polyvinylidene fluoride, and combinations thereof.

An example of a suitable non-woven polymer material may be a spunbond polyethylene terephthalate fabric, such as is commercially available as REEMAY® Style 2016 fabric (Kavon Filter Products Co., Farmingdale, N.J.). This fabric material is available in a variety of thicknesses and stiffnesses, and its surface has many contact points to enable strong attachment to a microporous diffusion membrane without occluding a majority of the pores on the attached membrane.

Another example of a non-woven polymer material suitable for use in the porous core may be a fabric containing layers of spunbond and meltblown polypropylene, such as is commercially available as WPT Nonwovens SB-201-45-SB fabric (WPT Nonwovens Corp., Beaver Dam, Ky.). This fabric material has a much lower porosity than the aforementioned REEMAY® Style 2016 fabric, which may aid in prevention of water intrusion to the core of the gas capsule in addition to providing support to the one or more diffusion membranes secured thereto.

Still another example of a non-woven polymer material suitable for use in the porous core may be a non-woven, flash-spun and heat-bonded high density polyethylene fabric, such as is commercially available as TYVEK® fabric (E.I du Pont de Nemours and Company, Wilmington, Del.). This fabric material is available in a variety of thicknesses and pore sizes and has been utilized widely in medical applications for sterile packaging.

Still yet another example of a non-woven polymer material suitable for use in the porous core may be a non-woven material composed of fibers with a polypropylene core and a low density polyethylene sheath, such as is commercially available as POREX® HRM 36777 (Porex Filtration Group Inc., Fairburn, Ga.). This structure enables laminate formation at temperatures that are compatible with a broad range of diffusion membranes and that do not collapse the structure provided by the polypropylene.

In a preferred embodiment, the porous core is a generally rectangular planar structure shaped to comprise two opposing surfaces and a periphery, and the at least one gas-permeable diffusion membrane comprises at least one gas-permeable diffusion membrane secured to each of the two opposing surfaces of the porous core. Alternatively, one of the two gas-permeable diffusion membranes may be replaced with a seal or other structure that does not allow gas to pass therethrough so that gas may diffuse from the porous core from only one of its two opposing surfaces.

The gas-permeable diffusion membrane may comprise a porous biocompatible material or a gas-permeable, non-porous biocompatible material. Where the gas-permeable diffusion membrane comprises a porous material, such a porous material may be a microporous membrane. Preferably, such a microporous membrane is a hydrophilic microporous membrane whose pores may be filled with water, from the local environment, during operation of the device. Use of such a hydrophilic membrane as the gas-permeable diffusion membrane may ensure that gas entering the porous core will first dissolve into the liquid trapped in the membrane and will then diffuse into the surrounding body tissue or encapsulated cells as long as the pressure within the porous core is kept below the bubble point of the gas-permeable diffusion membrane. It is preferable that undissolved gas is prevented from flowing through the membrane which could result in gas entrapment in an attached cell capsule or in the surrounding tissue.

Examples of microporous materials suitable for use as the gas-permeable diffusion membrane may include, but are not limited to, the following: microporous, hydrophilized expanded polytetrafluoroethylene (ePTFE) membranes, such as BIOPORE® membrane (Millipore Sigma, Burlington, Mass.); microporous, hydrophilic polyvinylidene fluoride (PVDF) membranes, such as DURAPORE® GVWP or DVPP membranes (MilliporeSigma, Burlington, Mass.); microporous, polyethersulfone membranes; microporous, polyethylene terephthalate track etch membranes that have been made hydrophilic by conjugation to polyvinylpyrrolidone or by plasma treatment (Sabeu, Cape Coral, Fla.); and microporous, hydrophilic polyethylene membranes, such as MIRAIM membranes (Teijin Limited, Tokyo, Japan).

Alternatively, where the gas-permeable diffusion membrane comprises a non-porous, gas-permeable material, such a material may be, for example, a thin silicone layer. In this case, gas may permeate through the gas-permeable diffusion membrane at a controlled rate and, thereafter, may dissolve into the aqueous environment on the exterior face of the gas-permeable diffusion membrane.

The gas-permeable diffusion membrane, itself, may be a single layer of monolithic structure or may be a laminate comprising a plurality of the materials described above and/or other layers which may provide one or more additional functionalities. An example of a membrane material that may include a plurality of layers to provide additional functionalities is the THERACYTE vascularizing membrane (TheraCyte, Inc., Laguna Hills, Calif.), which includes a hydrophilic cell-barrier layer, a layer that encourages close vascularization and integration with body tissues, and a structural layer.

The gas-permeable diffusion membrane may be secured to the porous core by being attached at multiple points to the porous core. In some embodiments, the gas-permeable diffusion membrane may be bonded directly to the porous core using a combination of heat and pressure. In some embodiments, the gas-permeable diffusion membrane may be bonded directly to the porous core using a solvent to soften the porous core material so that the gas-permeable diffusion membrane may be bonded to the porous core using pressure. In some embodiments, an adhesive may be used to bond the gas-permeable diffusion membrane to the porous core. In some embodiments, one or more layers, such as, but not limited to, a hydrophobic layer, may be interposed between the gas-permeable diffusion membrane and the porous core.

Preferably, the porous core is peripherally sealed to prevent the undesired escape of gas from within the porous core through the periphery of the porous core and to ensure that gases are delivered substantially through the one or more gas-permeable diffusion membranes. Such peripheral sealing may be effected in various manners. For example, the peripheral sealing may be effected by peripherally heat-sealing the gas-permeable diffusion membranes to one another, by peripherally heat-sealing the porous core so that the material of the porous core forms a perimeter seal and permeates the pores of the gas-permeable diffusion membranes, by peripherally heat-sealing the porous core so that the material of the porous core and the gas-permeable diffusion membranes form a monolithic seal, by peripherally heat-sealing the porous core, by using a thermoplastic gasket that flows into and/or around the edges of the porous core, by using a structural gasket, or by some combination of the above.

Preferably, the gas delivery device further comprises a gas supply member or other flow path through the periphery of the porous core for introducing gas into the interior of the porous core. The gas supply member may be a tube having one end inserted through the sealed periphery of the porous core and into the porous core and another end coupled to a gas source. Alternatively, the gas supply member may be any sort of via, conduit, channel, port, pathway or gas routing implement that may be used to introduce gas into the interior of the porous core. In some embodiments, more than one gas may be delivered to the porous core through multiple supply tubes or flow paths.

A gas delivery device that comprises the above-noted elements of a porous core, at least one gas-permeable diffusion membrane, a peripheral seal, and a gas supply member may be alternatively referred to herein as a gas diffuser or a scaffolded gas diffuser.

As noted above, gas may be generated outside of a body and then supplied to the gas delivery device percutaneously. Alternatively, gas may be stored or generated inside a body using an implanted medical device, such as a pressurized gas container, a chemical gas generator, an electrochemical gas generator, or a combination thereof, and such gas may be supplied to the gas delivery device through a flow path, such as a tube. Alternatively, the gas delivery device may be integrated with an implanted gas source.

For example, therapeutic hydrogen may be generated using an implantable water electrolyzer. The thus-generated hydrogen may then be supplied to the gas delivery device of the present invention, which, in turn, may deliver the hydrogen to local tissue or systemically via the circulatory system. In this example, waste oxygen may be diffused to the body using a second gas delivery device of the present invention, or the waste oxygen may be removed from the body percutaneously. Similarly, oxygen generated by an implanted water electrolyzer may be used as the therapeutic gas and be delivered to local tissue using the gas delivery device of the present invention, and waste hydrogen may be eliminated either using a second gas delivery device of the present invention or via a percutaneous device.

As described above, the gas delivery device of the present invention may function to safely dissipate waste gases by dissolving them in water. For example, where an implantable water electrolyzer is used to deliver oxygen to an implanted cell capsule, waste hydrogen gas generated by the water electrolyzer may be delivered to a gas delivery device of the present invention so that the waste hydrogen gas may be safely delivered to nearby tissue and the circulatory system, where it can be removed from the body by exhalation. The gas delivery device of the present invention may also be a component of a system that includes an implanted cell capsule and may function to safely deliver oxygen to the encapsulated cells.

With the gas delivery device of the present invention, gas is preferably delivered at a positive pressure relative to the surrounding tissue. The pressure differential may be in a range of between about 0.1 and 50 psi above ambient or blood pressure, depending on the application and on the design of the gas delivery system, i.e., the upper limit would be lower than the bubble point of the laminated membranes. The above-described gas delivery device preferably comprises a porous core that allows for maintenance of a uniform gas concentration throughout the porous core. The porous core is preferably bounded by a diffusion membrane on at least one surface. A gas supply member for supply of gas to the porous core may be provided. Some arrangement for sealing surfaces of the porous core to restrict gas flow may also be provided. Preferably, the diffusion membrane is bonded to the porous core at multiple points so that neither diffusion membrane nor the entire scaffolded diffuser device deforms substantially when gas is delivered within the pressure rating specified for the device. Bond strength should be sufficient to prevent delamination under the normal operating conditions of the device, which include not only the pressure differential between the inside and outside of the device, but also reasonable degrees and frequencies of other mechanical stresses (i.e., flexure, torsion, compression, shock) that will be expected in an implanted therapeutic device.

In certain embodiments, it may be desirable to exclude water present in the diffusion membrane from entering the porous core. This may be accomplished through one or more of the following: adjusting the properties of the diffusion membrane material; selecting non-wetting materials for the porous core; providing additional, intervening membrane layers which prevent liquid ingress to the porous core and maintain the relevant properties of the scaffolded gas diffuser (i.e., remain porous to gas and form a strong mechanical bond to both porous core and diffusion membrane elements). Where additional, intervening membrane layers are used, such layers may be, for example, one or more hydrophobic layers.

In certain embodiments, the scaffolded gas diffuser may be used to deliver a therapeutic gas, such as oxygen and/or hydrogen, to an integrated compartment or compartments that contain cellular therapeutics (e.g., encapsulated cells or tissues). In such embodiments, the scaffolded gas diffuser may serve to provide therapeutic gas to the cell compartment by diffusion through the diffusion membrane of the scaffolded gas diffuser. In such embodiments, the diffusion membrane may include features that improve the engraftment of encapsulated cells or tissues. Bonding of the diffusion membrane to the porous core medium may prevent deformation of the diffusion membrane, which may otherwise bow into the cell compartment, and encroach upon the encapsulated cells or tissues.

In certain embodiments, the cell capsule that is coupled to the gas delivery device may incorporate a spacer in its perimeter that allows a uniform height across the cell capsule. Such an arrangement may enable a more uniform distribution of cells and a more uniform delivery of therapeutic gases than is demonstrated in other gas-enabled cell capsules. In some cases, the scaffolded gas diffuser may be flanked by two integrated cell compartments, one on either side of the delivery device. In some cases, oxygen may be generated by an implanted water electrolyzer and may be supplied to the integrated cell capsules using the scaffolded gas diffuser. A second scaffolded gas diffuser without integrated cell capsules may be used to dissipate waste hydrogen safely so that it can be cleared from the body.

In certain embodiments, both a water electrolyzer and cell compartments may be integrated with the device. In some cases, the oxygen gas delivery may be achieved directly to the cell capsule, having its own vascularized tissue interface on one face, over a very short distance, and hydrogen may be allowed to diffuse into the tissue via a vascularized interface at the opposing face. Both interfaces may serve as sources of diffused water for supplying the electrolysis reaction which produces the hydrogen and oxygen. The present invention serves as an improvement to a previous integrated version of the cell implant system, as the interfaces between the oxygen gas compartment and cell capsule, as well as the hydrogen gas compartment and vascularized tissue interface, will be significantly better supported against any required pressure differential.

In certain embodiments, the implanted electrochemical oxygen generator may operate in such a way that hydrogen is not produced in the typical electrolysis cathode reaction. In such cases, the cathode reaction may involve an electrochemical reduction of extant tissue-dissolved oxygen, oxygen delivered by diffusion via a percutaneous air interface, or a co-implanted (single-use only) metal oxide or other oxidizer.

Figure 1B:
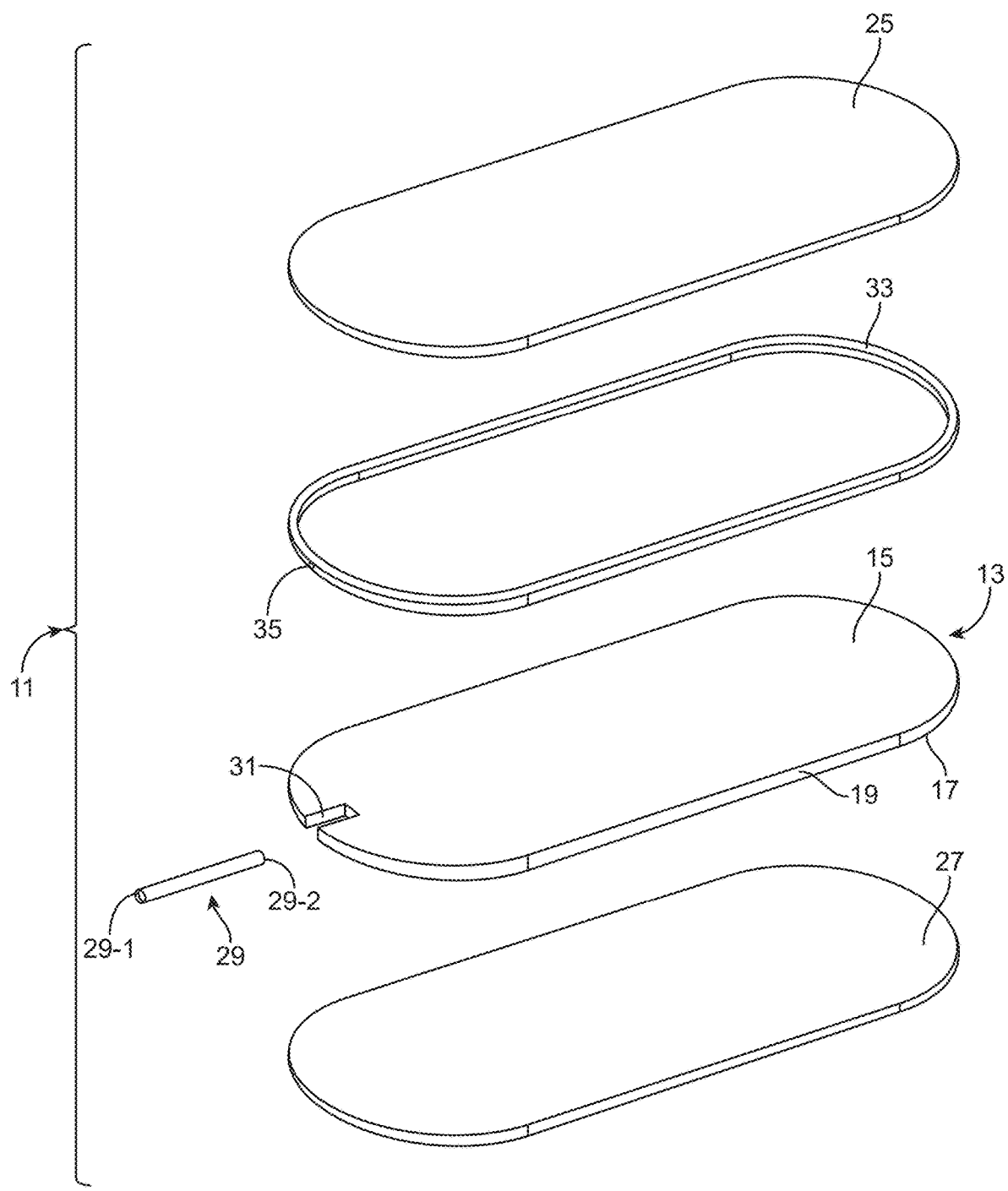

Referring now to FIGS. 1A and 1B, there are shown various views of a first embodiment of a gas delivery device constructed according to the present invention, the gas delivery device being represented generally by reference numeral 11. (For simplicity and clarity, certain aspects of gas delivery device 11 that are not critical to an understanding of the present invention are either not shown or described herein or are shown and/or described herein in a simplified manner.)

Gas delivery device 11 may comprise a porous core 13. Porous core 13 may be formed from any of the porous core materials described above so as to allow the rapid equilibration of gas therethrough via diffusion and/or convection. Although porous core 13 is shown in the present embodiment as having a monolithic structure made of a single layer, it is to be understood that porous core 13 need not be so constructed and may be a composite structure made of a plurality of layers and/or made of a plurality of materials. In the present embodiment, porous core 13 is a generally planar, oval-shaped structure comprising a top surface 15, a bottom surface 17, and a periphery 19, periphery 19 extending between top surface 15 and bottom surface 17. However, it is to be understood that the shape of porous core 13 is merely illustrative and that porous core 13 may assume other shapes.

Gas delivery device 11 may further comprise a first diffusion membrane 25 and a second diffusion membrane 27. Each of first diffusion membrane 25 and second diffusion membrane 27 may be formed from any of the gas-permeable diffusion membrane materials described above. In the present embodiment, first diffusion membrane 25 and second diffusion membrane 27 may be identical in composition and structure to one another, but they need not be. (In fact, one of diffusion membranes 25 and 27 could be replaced with a seal if one wishes gas to exit porous core 13 through only one of membranes 25 and 27.) First diffusion membrane 25 and second diffusion membrane 27 may have footprints substantially matching that of top surface 15 and bottom surface 17, respectively, of porous core 13, and first diffusion membrane 25 and second diffusion membrane 27 may be bonded or otherwise fixed to top surface 15 and bottom surface 17, respectively, of porous core 13, by any suitable technique, such as, but not limited to, by adhesive, by point-welding the materials, or by laminating.

Gas delivery device 11 may further comprise a supply tube 29. Supply tube 29, which may be used to supply gas to porous core 13 from a gas source (not shown), may be a tubular member having a first end 29-1 and a second end 29-2. First end 29-1 may be coupled to the gas source. Second end 29-2 may be inserted, for example, through periphery 19 into a notch 31 provided in porous core 13 and may be secured within porous core 13.

Gas delivery device 11 may further comprise a sealing gasket 33. Sealing gasket 33, which may be made of a non-porous, gas-impermeable material, may be secured to periphery 19 of porous core 13 by any suitable technique. Sealing gasket 33 may function to ensure that gas introduced into porous core 13 through supply tube 29 does not exit through periphery 19 and, instead, exits through diffusion membranes 25 and 27. Sealing gasket 33 may be shaped to include an opening 35 through which supply tube 29 may be inserted.

Gas delivery device 11 may be used in any of the ways described above. For example, diffusion membranes 25 and/or 27 may be positioned in contact with or in close proximity to a location to which the delivery of gas is desired. More specifically, if one wishes to supply gas to one or more cell capsules, gas delivery device 11 may be situated so that diffusion membranes 25 and/or 27 are placed in contact with or in close proximity to said one or more cell capsules. Alternatively or additionally, if one wishes to supply gas directly to cells or tissues in a native environment, either for a therapeutic purpose or to expel the gas from a patient, gas delivery device 11 may be situated so that diffusion membranes 25 and/or 27 are in contact with or in close proximity to such native cells or tissues.

As can be appreciated, because porous core 13 is preferably constructed to have a high tensile strength and because diffusion membranes 25 and 27 are securely bonded to porous core 13, gas delivery device 11 is capable of withstanding significant pressurization without deformation. Moreover, because diffusion membranes 25 and 27 preferably are made of a hydrophilic material that causes the gas to be released therefrom while dissolved in water or, alternatively, are made of a non-porous, gas-permeable material that causes the gas to be slowly released therefrom, the delivery of gas from device 11 can be effected in a more controlled manner.

Figure 2A:
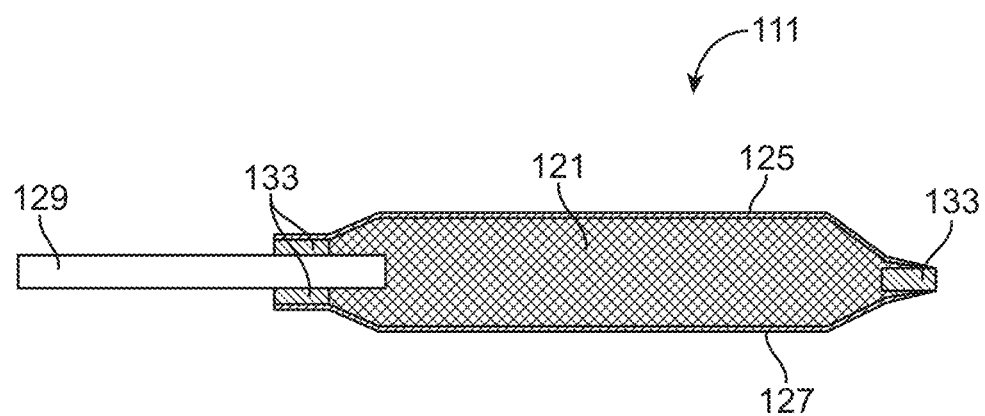
FIG. 2A is a simplified section view of a second embodiment of a gas delivery device constructed according to the present invention.

Referring now to FIG. 2A, there is shown a simplified section view of a second embodiment of a gas delivery device constructed according to the present invention, the gas delivery device being represented generally by reference numeral 111. (For simplicity and clarity, certain aspects of gas delivery device 111 that are not critical to an understanding of the present invention are either not shown or described herein or are shown and/or described herein in a simplified manner.)

Gas delivery device 111 may be similar in many respects to gas delivery device 11. For example, gas delivery device 111 may comprise a porous core 121 generally similar to porous core 13, a first diffusion membrane 125 generally similar to first diffusion membrane 25, a second diffusion membrane 127 generally similar to second diffusion membrane 27, and a supply tube 129 generally similar to supply tube 29, wherein first diffusion membrane 125 may be secured to a top surface of porous core 121, second diffusion membrane 127 may be secured to a bottom surface of porous core 121, and supply tube 129 may be inserted into porous core 121 through the periphery of porous core 121. However, in contrast with gas delivery device 11, gas delivery device 111 does not include a sealing gasket 33. Instead, the materials used to form porous core 121, first diffusion membrane 125, and second diffusion membrane 127 may be preferably selected so that the melting temperature of porous core 121 is lower than that of first diffusion membrane 125 and second diffusion membrane 127. In this manner, porous core 121 may be selectively melted at its periphery to form a gas-tight seal 133 around both supply tube 129 and between first diffusion membrane 125 and second diffusion membrane 127. If desired, supply tube 129 may be made of a material with a similar melting temperature to porous core 121 to ensure a uniform seal therebetween. Alternatively, supply tube 129 may have a higher melting point than porous core 121. A non-melting object, such as a stainless steel pin gauge or a polytetrafluoroethylene (PTFE) filament, may be inserted in supply tube 129 during fabrication of gas delivery device 111 to ensure that a flow path remains after diffusion membrane bonding and formation of the perimeter seal.

Figure 2B:
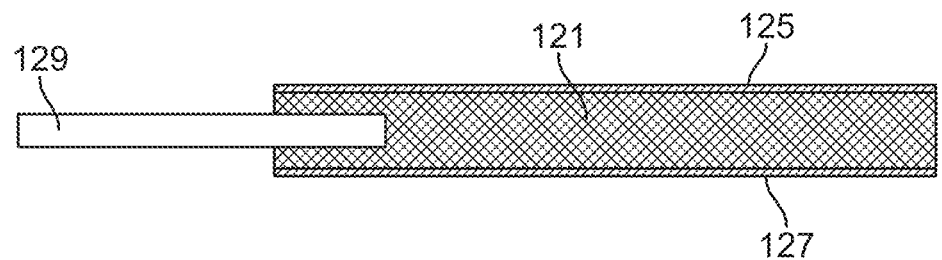
FIG. 2B is a simplified section view of the gas delivery device of FIG. 2A prior to the heat-sealing of the porous core around its periphery.

Referring now to FIG. 2B, porous core 121, first diffusion membrane 125, second diffusion membrane 127, and supply tube 129 are shown prior to the melting of porous core 121 to form gas-tight seal 133.

Figure 3A:
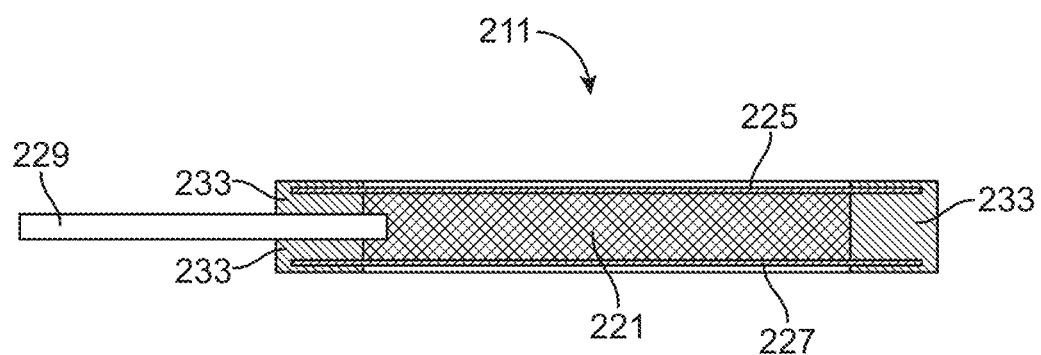
FIG. 3A is a simplified section view of a third embodiment of a gas delivery device constructed according to the present invention.

Referring now to FIG. 3A, there is shown a simplified section view of a third embodiment of a gas delivery device constructed according to the present invention, the gas delivery device being represented generally by reference numeral 211. (For simplicity and clarity, certain aspects of gas delivery device 211 that are not critical to an understanding of the present invention are either not shown or described herein or are shown and/or described herein in a simplified manner.)

Figure 3B:
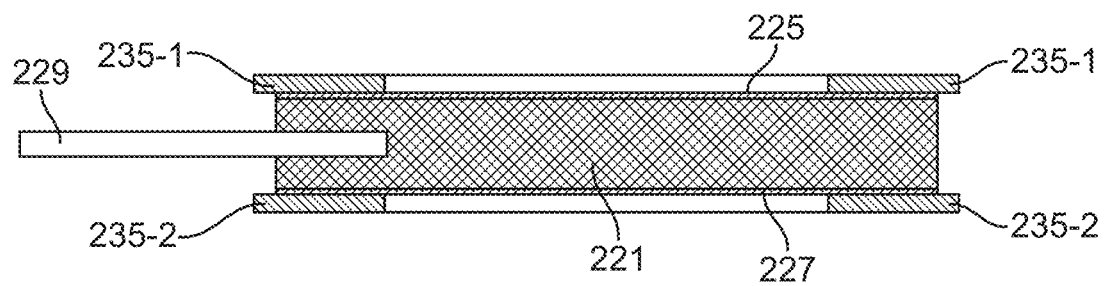
FIG. 3B is a simplified section view of the gas delivery device of FIG. 3A prior to the heat-sealing of the thermoplastic gasket.

Gas delivery device 211 may be similar in many respects to gas delivery device 11. For example, gas delivery device 211 may comprise a porous core 221 generally similar to porous core 13, a first diffusion membrane 225 generally similar to first diffusion membrane 25, a second diffusion membrane 227 generally similar to second diffusion membrane 27, and a supply tube 229 generally similar to supply tube 29, wherein first diffusion membrane 225 may be secured to a top surface of porous core 221, second diffusion membrane 227 may be secured to a bottom surface of porous core 221, and supply tube 229 may be inserted into porous core 221 through the periphery of porous core 121. However, in contrast with gas delivery device 11, gas delivery device 211 does not include a sealing gasket 33. Instead, gas delivery device 211 may comprise a sealing gasket 233 that seals the periphery of porous core 221. As seen best in FIG. 3B, sealing gasket 233 may be formed by melting a pair of thermoplastic members 235-1 and 235-2. Thermoplastic member 235-1, which may be a track-shaped structure, may be positioned over first diffusion membrane 225 and may extend slightly beyond the respective peripheries of porous core 221 and first diffusion membrane 225. Similarly, thermoplastic member 235-2, which may be identical in size, shape and composition to thermoplastic member 235-1, may be positioned under second diffusion member 227 and may extend slightly beyond the respective peripheries of porous core 221 and second diffusion member 227. By directing energy at thermoplastic members 235-1 and 235-2, thermoplastic members 235-1 and 235-2 may be caused to melt into one another and both to fill the pores at the periphery of porous core 221 (as well as the pores at the respective peripheries of first diffusion member 225 and second diffusion member 227) and to adhere to the supply tube 229 to form a gas-tight seal. As can be appreciated, in order to facilitate the penetration of thermoplastic members 235-1 and 235-2 into porous core 221, first diffusion member 225 and second diffusion member 227 are preferably porous.

Figure 4A:
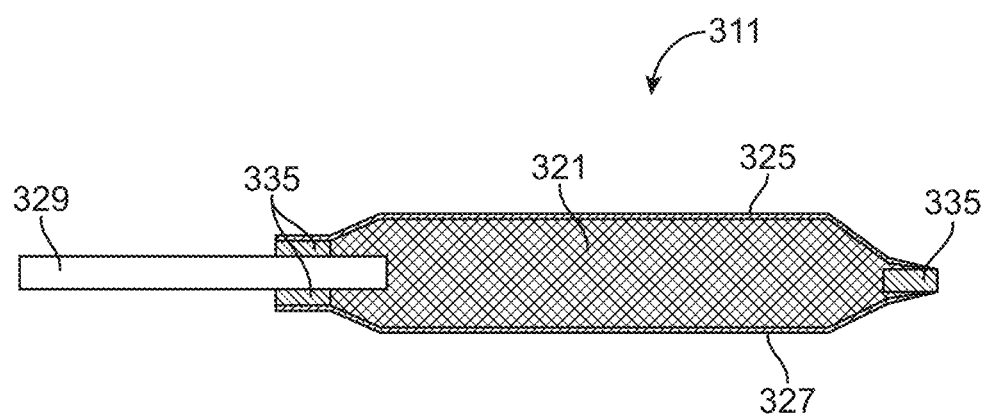
FIG. 4A is a simplified section view of a fourth embodiment of a gas delivery device constructed according to the present invention.

Referring now to FIG. 4A, there is shown a simplified section view of a fourth embodiment of a gas delivery device constructed according to the present invention, the gas delivery device being represented generally by reference numeral 311. (For simplicity and clarity, certain aspects of gas delivery device 311 that are not critical to an understanding of the present invention are either not shown or described herein or are shown and/or described herein in a simplified manner.)

Figure 4B:
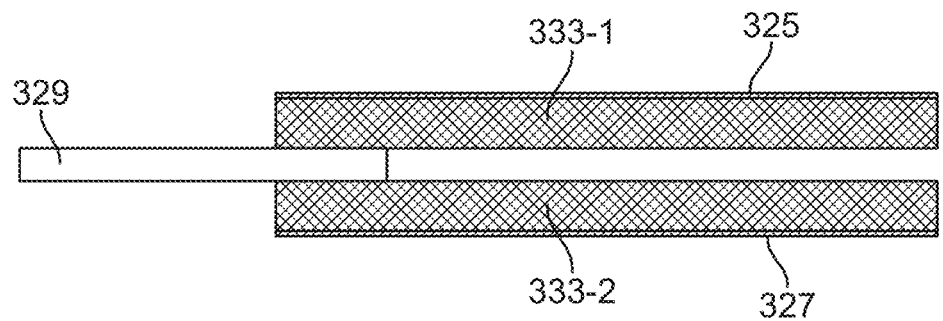
FIG. 4B is a simplified section view of the gas delivery device of FIG. 4A prior to heat-sealing.

Gas delivery device 311 may be similar in many respects to gas delivery device 111. For example, gas delivery device 311 may comprise a porous core 321 generally similar to porous core 121, a first diffusion membrane 325 generally similar to first diffusion membrane 125, a second diffusion membrane 327 generally similar to second diffusion membrane 127, and a supply tube 329 generally similar to supply tube 129. A principal difference between gas delivery device 311 and gas delivery device 111 may reside in the respective manners in which gas delivery devices 311 and 111 may be manufactured. As seen best in FIG. 4B, the subject gas delivery device may be assembled by providing a pair of porous core layers 333-1 and 333-2, between which supply tube 329 may be inserted. Porous core layers 333-1 and 333-2 may be identical to one another, and each may be made of a non-woven material composed of two different thermoplastics. An example of such a non-woven material is HRM 36777 (Porex Filtration Group Inc., Fairburn, Ga.), which is formed from a polypropylene core fiber with a polyethylene coating or sheath. An initial application of thermal energy may be used to bond diffusion membrane 325 to porous core layer 333-1 and to bond diffusion membrane 327 to porous core layer 333-2, as well as to bond porous core layers 333-1 and 333-2 to one another to form porous core 321. A second application of energy directed to the perimeter may then be used to melt both thermoplastic components of porous core 321 to form a perimeter seal 335. This arrangement eases assembly as it provides protection of the diffusion membranes 325 and 327 from the edges of supply tube 329 during manufacture.

Figure 5A:
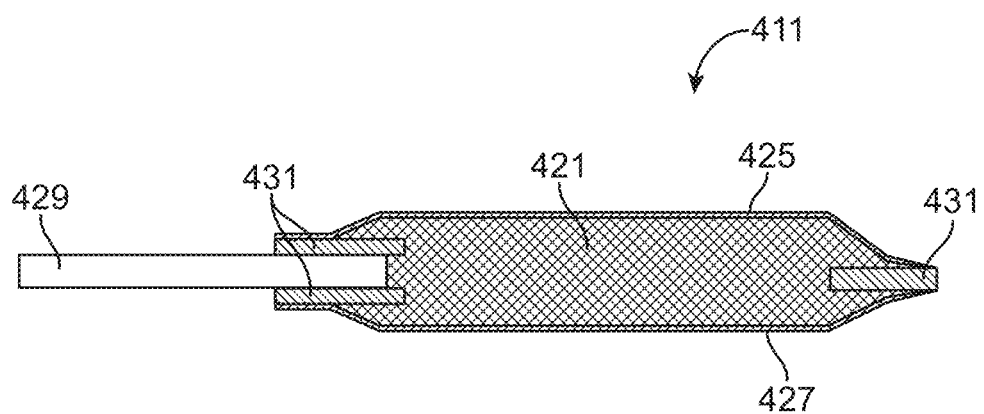
FIG. 5A is a simplified section view of a fifth embodiment of a gas delivery device constructed according to the present invention.

Referring now to FIG. 5A, there is shown a simplified section view of a fifth embodiment of a gas delivery device constructed according to the present invention, the gas delivery device being represented generally by reference numeral 411. (For simplicity and clarity, certain aspects of gas delivery device 411 that are not critical to an understanding of the present invention are either not shown or described herein or are shown and/or described herein in a simplified manner.)

Figure 5B:
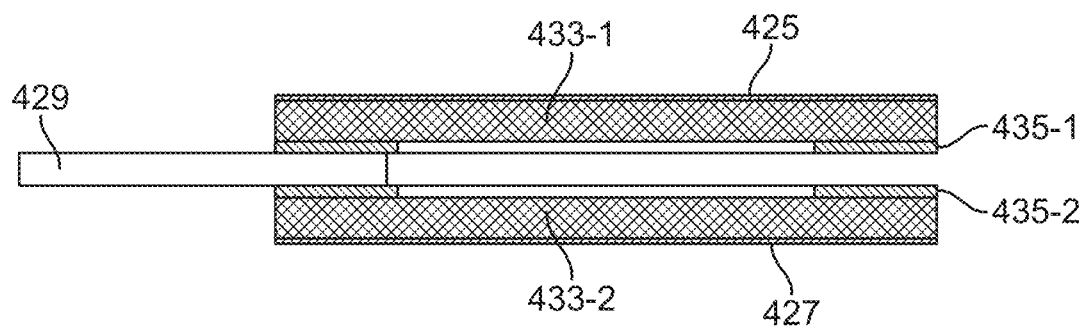
FIG. 5B is a simplified section view of the gas delivery device of FIG. 5A prior to heat-sealing.

Gas delivery device 411 may be similar in many respects to gas delivery device 311. For example, gas delivery device 411 may comprise a porous core 421 generally similar to porous core 321, a first diffusion membrane 425 generally similar to first diffusion membrane 325, a second diffusion membrane 427 generally similar to second diffusion membrane 327, and a supply tube 429 generally similar to supply tube 329. A principal difference between gas delivery device 411 and gas delivery device 311 may be that gas delivery device 411 may comprise a sealing gasket 431 formed by the fusion of two thermoplastic members. As seen best in FIG. 5B, the subject gas delivery device may be assembled by providing a pair of porous core layers 433-1 and 433-2, between which supply tube 429 and thermoplastic members 435-1 and 435-2 may be inserted. Thermal energy may be used to bond diffusion membrane 425 to porous core layer 433-1, to bond diffusion membrane 427 to porous core layer 433-2, as well as to bond porous core layers 433-1 and 433-2 to one another to form porous core 421 and to bond thermoplastic members 435-1 and 435-2 to one another and around supply tube 429 to form sealing gasket 431.

Figure 6A:
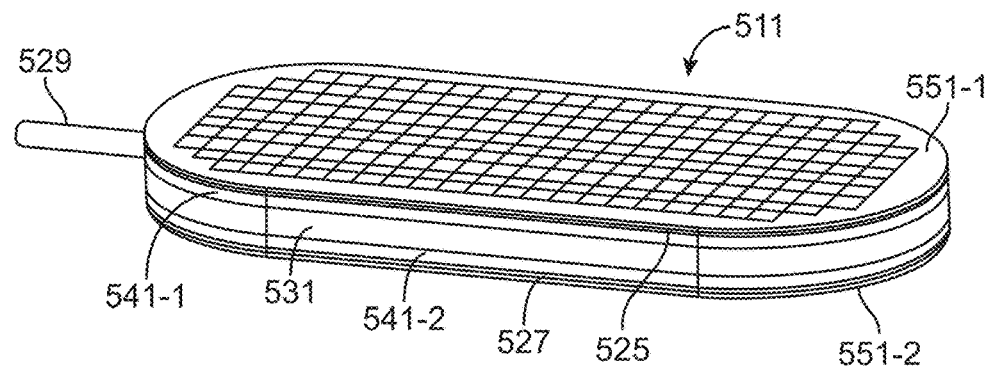
FIG. 6A is a simplified perspective view of a sixth embodiment of a gas delivery device constructed according to the present invention.
Figure 6B:
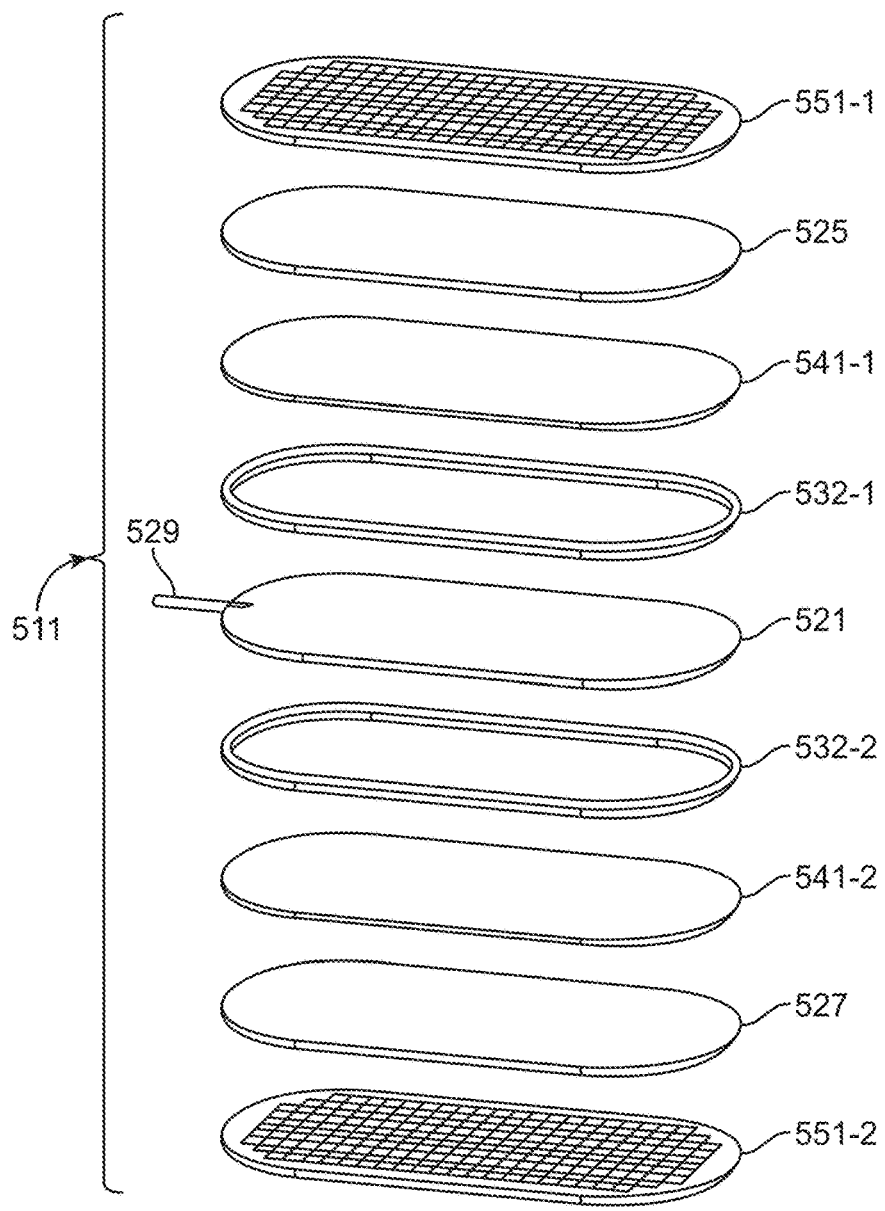
FIG. 6B is a simplified exploded perspective view of the gas delivery device of FIG. 6A prior heat-sealing.

Referring now to FIGS. 6A and 6B, there are shown various views of a sixth embodiment of a gas delivery device constructed according to the present invention, the gas delivery device being represented generally by reference numeral 511. (For simplicity and clarity, certain aspects of gas delivery device 511 that are not critical to an understanding of the present invention are either not shown or described herein or are shown and/or described herein in a simplified manner.)

Gas delivery device 511 may be similar in certain respects to gas delivery device 11. For example, gas delivery device 511 may comprise a porous core 521 (see FIG. 6B) generally similar to porous core 13, a first diffusion membrane 525 generally similar to first diffusion membrane 25, a second diffusion membrane 527 generally similar to second diffusion membrane 27, and a supply tube 529 generally similar to supply tube 29. Porous core 521 preferably comprises one or more materials that enable bonding to adjacent components of gas delivery device 511.

Gas delivery device 511 may differ from gas delivery device 11 in that gas delivery device 511 may further comprise a thermoplastic gasket 531 (see FIG. 6A), which may be formed by melting together a first thermoplastic member 532-1 (see FIG. 6B) positioned directly on top of porous core 521 and a second thermoplastic member 532-2 (see FIG. 6B) positioned directly under porous core 521. Thermoplastic members 532-1 and 532-2 may be similar to thermoplastic members 235-1 and 235-2 of gas delivery device 211.

In addition, gas delivery device 511 may further differ from gas delivery device 11 in that gas delivery device 511 may further comprise a first hydrophobic membrane 541-1 and a second hydrophobic membrane 541-2. Prior to melting thermoplastic members 532-1 and 532-2, first hydrophobic membrane 541-1 may be positioned between first diffusion membrane 525 and thermoplastic member 532-1, and second hydrophobic membrane 541-2 may be positioned between second diffusion membrane 527 and thermoplastic member 532-2. First hydrophobic membrane 541-1 and second hydrophobic membrane 541-2 may serve to keep water from penetrating porous core 521, particularly where diffusion membranes 525 and 527 comprise hydrophilic materials. Hydrophobic membranes 541-1 and 541-2 may comprise one or more hydrophobic or superhydrophobic materials. Examples of materials suitable for use as hydrophobic membranes 541-1 and 542-2 may include, but are not limited to, SUPOR®-450R or SUPOR®-200R membrane filters (Pall Corporation, Port Washington, N.Y.) or SUREVENT® superhydrophobic PVDF membranes (Millipore Sigma, Burlington, Mass.).

Additionally, gas delivery device 511 may further differ from gas delivery device 11 in that gas delivery device 511 may further comprise a first tissue integration layer 551-1, which may be positioned over first diffusion membrane 525, and a second tissue integration layer 551-2, which may be positioned under second diffusion membrane 527. First tissue integration layer 551-1 and second tissue integration layer 551-2 may serve to promote close vascularization with native tissue while inhibiting fibrotic encapsulation. Examples of materials suitable for use as tissue integration layers 551-1 and 551-2 may include, but are not limited to, the vascularizing membranes disclosed in U.S. Patent Application Publication No. US 2015/0112247 A1.

The bonding together of one or more of the layers of gas delivery device 511 may be effected using one or more of a variety of techniques including, but not limited to, the application of heat and pressure; ultrasonic welding; and the use of a bonding agent, such as a medical grade adhesive. Diffusion membrane 525 may be bonded to hydrophobic membrane 541-1, and diffusion membrane 527 may be bonded to hydrophobic membrane 541-2, to form a pair of laminates prior to bonding these laminates to porous core 521. In the present embodiment, heat is preferably applied to thermoplastic members 532-1 and 532-2 so that thermoplastic members 532-1 and 532-2 melt into adjacent areas of porous core 521 so as to form a perimeter seal around the device. Thermoplastic members 532-1 and 532-2 may also melt into adjacent areas of their respective diffusion membranes 525 and 527 and hydrophobic membranes 541-1 and 541-2 to further peripherally seal the device.

Gas delivery device 511 may be particularly well-suited for delivering a gas, such as hydrogen, to the circulatory system of a patient, for example, either to have the gas disseminated systemically throughout the patient's body, for example, where the gas is intended as a therapeutic agent, or to have the gas expelled through the patient's lungs, for example, where the gas is viewed as a waste gas. In particular, the use of gas delivery device 511 to deliver a therapeutic gas, such as hydrogen, to a patient's circulatory system for systemic dissemination is believed to be of considerable benefit. By comparison, inhalation, a current technique for delivering gaseous hydrogen, can lead to significant variability in efficacy of delivery depending on the respiration rate of the patient (Ono et al., "A Basic Study on Molecular Hydrogen (H2) Inhalation in Acute Cerebral Ischemia Patients for Safety Check with Physiological Parameters and Measurement of Blood H2 Level," *Med. Gas Res.*, 2:21 (2012)). There is also a safety concern with inhalation as a delivery technique as hydrogen mixed with air becomes an explosion hazard when the relative concentration of hydrogen reaches 4% in air at atmospheric pressures. A safer alternative is to dissolve hydrogen in aqueous media and to deliver either via ingestion or via saline drip. However, variability of dosing is a challenge for both methods since different subjects may consume a hydrogen-saturated beverage at different rates and may have different levels of uptake. Moreover, saline drip is impractical for patients who are ambulatory.

By comparison, gas delivery device 511, as well as the other gas delivery devices discussed herein, addresses the need to safely deliver therapeutic gases to the body, and enables tightly controlled dosing, for example, by delivering hydrogen subcutaneously either using an external, pressurized source or an implanted water electrolyzer. Hydrogen gas may be delivered to the body under pressure in accordance with the invention. In some embodiments, the gas delivery device is flexible and sufficiently thin and otherwise proportioned as to be amenable to patient comfort and to standard surgical implantation techniques. For example, the gas delivery device, such as gas delivery device 511, may have an overall thickness of about 0.2 mm to 10 mm, preferably less than 3 mm, and may have an overall surface area in the range of about 1-100 cm$^2$. It is critically important for safety that the gas delivery device release the gas in a controlled manner and that it not be susceptible to deformation or rupture under pressure. Hydrogen would be expected to permeate a hydrophilic layer within the device and diffuse through the vascularizing and tissue interface layers into the body, where it would ultimately enter the vasculature for systemic distribution and ultimately for elimination by exhalation. In another example, it may be desirable to deliver gaseous oxygen or other therapeutic gases, such as nitric oxide or hydrogen sulfide, directly to tissues inside the body. It is important to note that the invention may be used for delivery of any gas to body tissue.

Figure 7:
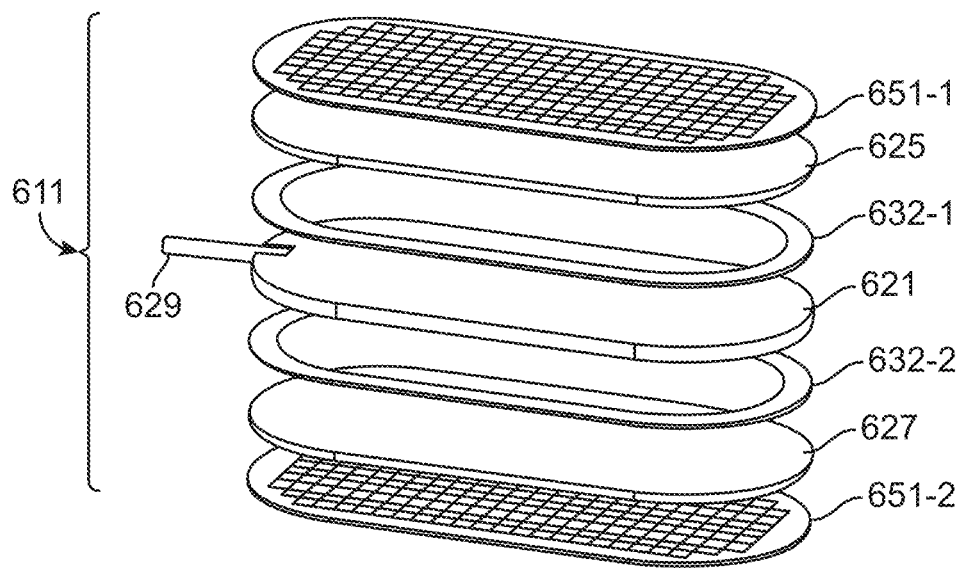
FIG. 7 is a simplified exploded perspective view of a seventh embodiment of a gas delivery device constructed according to the present invention, the gas delivery device being shown prior to heat-sealing.

Referring now to FIG. 7, there is shown a seventh embodiment of a gas delivery device constructed according to the present invention, the gas delivery device being represented generally by reference numeral 611. (For simplicity and clarity, certain aspects of gas delivery device 611 that are not critical to an understanding of the present invention are either not shown or described herein or are shown and/or described herein in a simplified manner.)

Gas delivery device 611 may be similar in many respects to gas delivery device 511. For example, gas delivery device 611 may comprise a porous core 621 generally similar to porous core 521, thermoplastic members 632-1 and 632-2 generally similar to thermoplastic members 532-1 and 532-2, respectively, tissue integration layers 651-1 and 651-2 generally similar to tissue integration layers 551-1 and 551-2, respectively, and a supply tube 629 generally similar to supply tube 529.

Gas delivery device 611 may differ from gas delivery device 511 in that, instead of including both diffusion membranes 525 and 527 and hydrophobic membranes 541-1 and 541-2, gas delivery device 611 may comprise diffusion membranes 625 and 627 that may serve both to exclude water from entering porous core 621 and to provide controlled diffusion of gases, such as hydrogen to the body. To this end, one or both of diffusion membranes 625 and 627 may be a laminate structure comprising a hydrophobic layer similar to hydrophobic membranes 541-1 and 541-2 of gas delivery device 511 and a diffusion layer similar to diffusion membranes 525 and 527 of gas delivery device 511. Alternatively, one or both of diffusion membranes 625 and 627 may comprise a single layer possessing the functionalities of both hydrophobic membranes 541-1 and 541-2 and diffusion membranes 525 and 527. One possible material possessing both functionalities would be a non-porous silicone membrane. The lack of pores in such a membrane would prevent most liquids from reaching a porous core coupled thereto. With such a membrane, gases, such as hydrogen, would dissolve first into the silicone membrane and then into the interstitial fluid or into the water in the tissue integration layer of the device.

Figure 8:
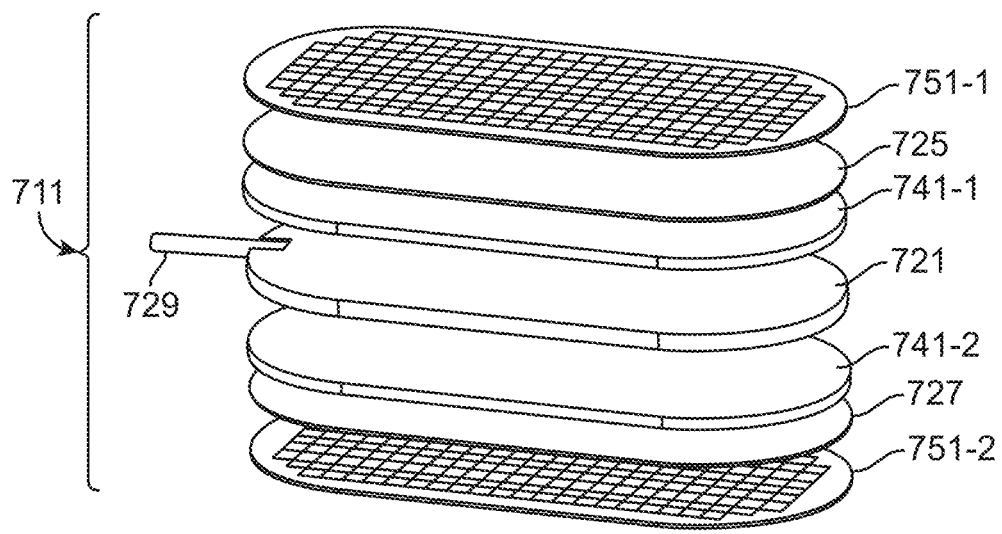
FIG. 8 is a simplified exploded perspective view of an eighth embodiment of a gas delivery device constructed according to the present invention, the gas delivery device being shown prior to heat-sealing.

Referring now to FIG. 8, there is shown an eighth embodiment of a gas delivery device constructed according to the present invention, the gas delivery device being represented generally by reference numeral 711. (For simplicity and clarity, certain aspects of gas delivery device 711 that are not critical to an understanding of the present invention are either not shown or described herein or are shown and/or described herein in a simplified manner.)

Gas delivery device 711 may be similar in many respects to gas delivery device 511. For example, gas delivery device 711 may comprise a porous core 721 generally similar to porous core 521, diffusion membranes 725 and 727 generally similar to diffusion membranes 525 and 527, respectively, hydrophobic membranes 741-1 and 741-2 generally similar to diffusion membranes 541-1 and 541-2, respectively, tissue integration layers 751-1 and 751-2 generally similar to tissue integration layers 551-1 and 551-2, respectively, and a supply tube 729 generally similar to supply tube 529.

Gas delivery device 711 may differ from gas delivery device 511 in that gas delivery device 711 may lack a thermoplastic gasket formed by melting together a first thermoplastic member positioned directly on top of the porous core and a second thermoplastic member positioned directly under the porous core. Instead, in gas delivery device 711, hydrophobic membranes 741-1 and 741-2 may be bonded directly to porous core 721. Such bonding may be effected by any one or more of a variety of techniques including: the application of heat and pressure; ultrasonic welding; or the use of a bonding agent, such as a medical grade adhesive. Consequently, in gas delivery device 711, rather than sealing the perimeter using a thermoplastic gasket, sealing is achieved by delivery of sufficient energy to the device perimeter to cause the material forming porous core 721 to melt, thus forming a gas-tight perimeter seal. For example, if the porous core were formed using a thermoplastic, such as polyethylene or polypropylene, the thermoplastic could be caused to melt and collapse at the perimeter using technologies, such as ultrasonic welding or heat staking.

Figure 9:
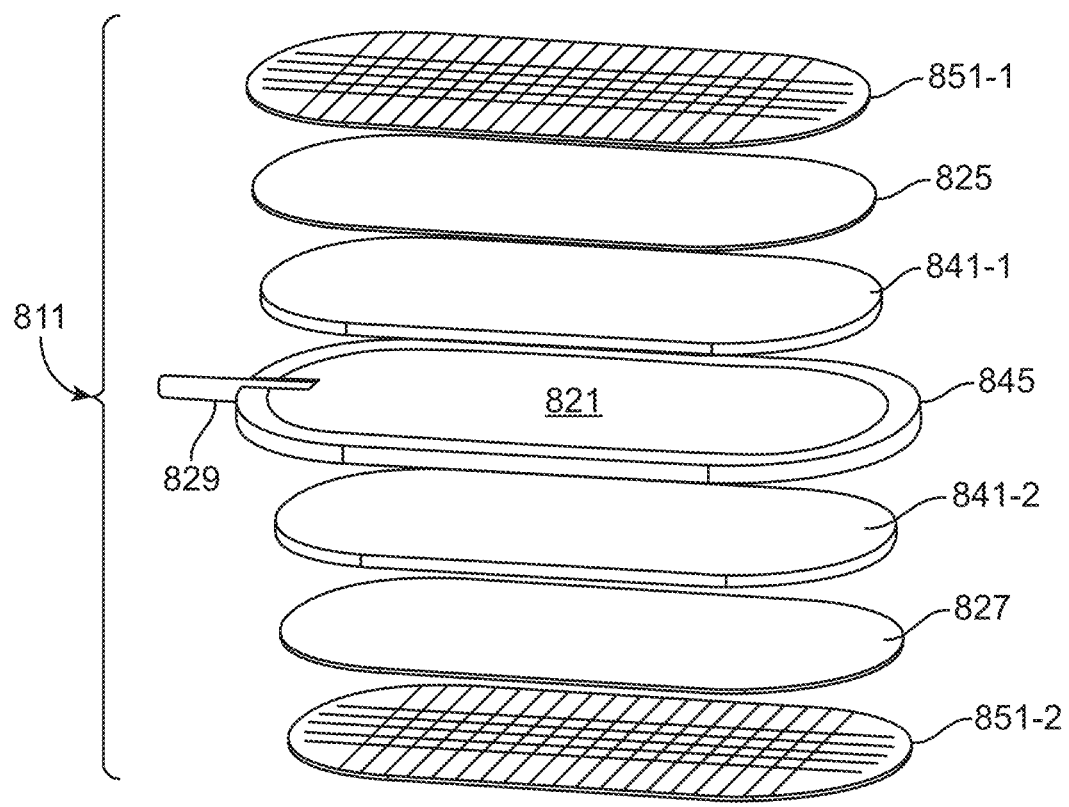
FIG. 9 is a simplified exploded perspective view of a ninth embodiment of a gas delivery device constructed according to the present invention, the gas delivery device being shown prior to heat-sealing.

Referring now to FIG. 9, there is shown a ninth embodiment of a gas delivery device constructed according to the present invention, the gas delivery device being represented generally by reference numeral 811. (For simplicity and clarity, certain aspects of gas delivery device 811 that are not critical to an understanding of the present invention are either not shown or described herein or are shown and/or described herein in a simplified manner.)

Gas delivery device 811 may be similar in many respects to gas delivery device 711. For example, gas delivery device 811 may comprise a porous core 821 generally similar to porous core 721, diffusion membranes 825 and 827 generally similar to diffusion membranes 725 and 727, respectively, hydrophobic membranes 841-1 and 841-2 generally similar to diffusion membranes 741-1 and 741-2, respectively, tissue integration layers 851-1 and 851-2 generally similar to tissue integration layers 751-1 and 751-2, respectively, and a supply tube 829 generally similar to supply tube 729.

Gas delivery device 811 may differ from gas delivery device 711 in that gas delivery device 811 may further comprise a thermoplastic gasket 845 peripherally surrounding porous core 821. Although supply tube 829 is shown inserted through gasket 845 into porous core 821, supply tube 829 and gasket 845 could be integrated. The structure of gasket 845 serves to form a perimeter seal around porous core 821 and may be fabricated from materials that minimize compression during heating but still have sufficient melt flow, if desired, to seal the pore structures at the perimeters of the diffusion and hydrophobic membranes. In one embodiment, gasket 845 may be formed using a low-melting temperature polymer with non-melting fiber reinforcement. For example, a high density, non-woven polyester mesh can be permeated with a lower-melting temperature polymer, such as polyethylene. When heat and pressure are applied to such a structure, the polyester mesh will act to maintain a predictable gasket thickness while some of the polyethylene melts into the edges of the adjacent porous core and hydrophobic and diffusion membranes. Alternatively, gasket 845 may be formed from a sintered material with a comparatively high melting temperature, such as POREX® XS-96193 UHMWPE sintered material (Porex Corporation, Fairburn, Ga.), that has been permeated by a lower melting temperature polymer, such as low density polyethylene. During thermal processing, the UHMWPE will maintain a predictable gasket thickness while some of the low density polyethylene melts into the edges of the adjacent layers. Advantages of this design include a reduced likelihood of gas tube occlusion during fabrication and a reduced likelihood of perimeter leaks.

As can be seen, the gas delivery device of the present invention may have a flat form factor that allows flexibility for patient comfort, while providing sufficient rigidity in the main plane of the device to prevent significant swelling or distortion of the device. This design, in addition to improving patient comfort, can improve device safety by providing a high density of bonding points between diffusive surfaces and the core structural material. Also, in contrast to existing devices, the gas delivery device of the present invention can function as an independent device for safe delivery of therapeutic gases to tissues inside the body.

As noted above, the present invention is directed not only at a gas delivery device but also at various systems or assemblies that include such a gas delivery device in combination with other structures. For example, the gas delivery device of the present invention may be complexed with various types of capsules containing implanted cells and/or tissues (such implanted cells and/or tissues also sometimes referred to herein as "cellular therapeutics"). In certain embodiments, the gas diffusion device may be used to deliver therapeutic gas, such as oxygen and/or hydrogen, to such a capsule containing cellular therapeutics. As one example, it may be desirable to transplant tissue, such as pancreatic islets, into a subject. The tissue may be protected from the immune system using selectively permeable membranes which allow nutrients from the body to reach the implant and also allow therapeutic substances produced by the implanted tissue to reach the body. In this example, unassisted oxygen availability to the implanted tissue may be insufficient to maintain tissue health and function. Gaseous oxygen may be delivered to a gas delivery device that provides controlled transport of oxygen to the cell capsule. The present invention, when integrated with cell capsules, enables safe, controlled delivery of oxygen to the integrated cell capsules. In these embodiments, the present invention serves to provide therapeutic gas to the cell compartment by diffusion through the diffusion membrane of the gas delivery device. In these embodiments, the diffusion membrane may include features that improve the engraftment of encapsulated tissues. Bonding of the diffusion membrane to the porous core prevents deformation of the diffusion membrane that would otherwise bow into the cell compartment and encroach upon the encapsulated cells.

Figure 10:
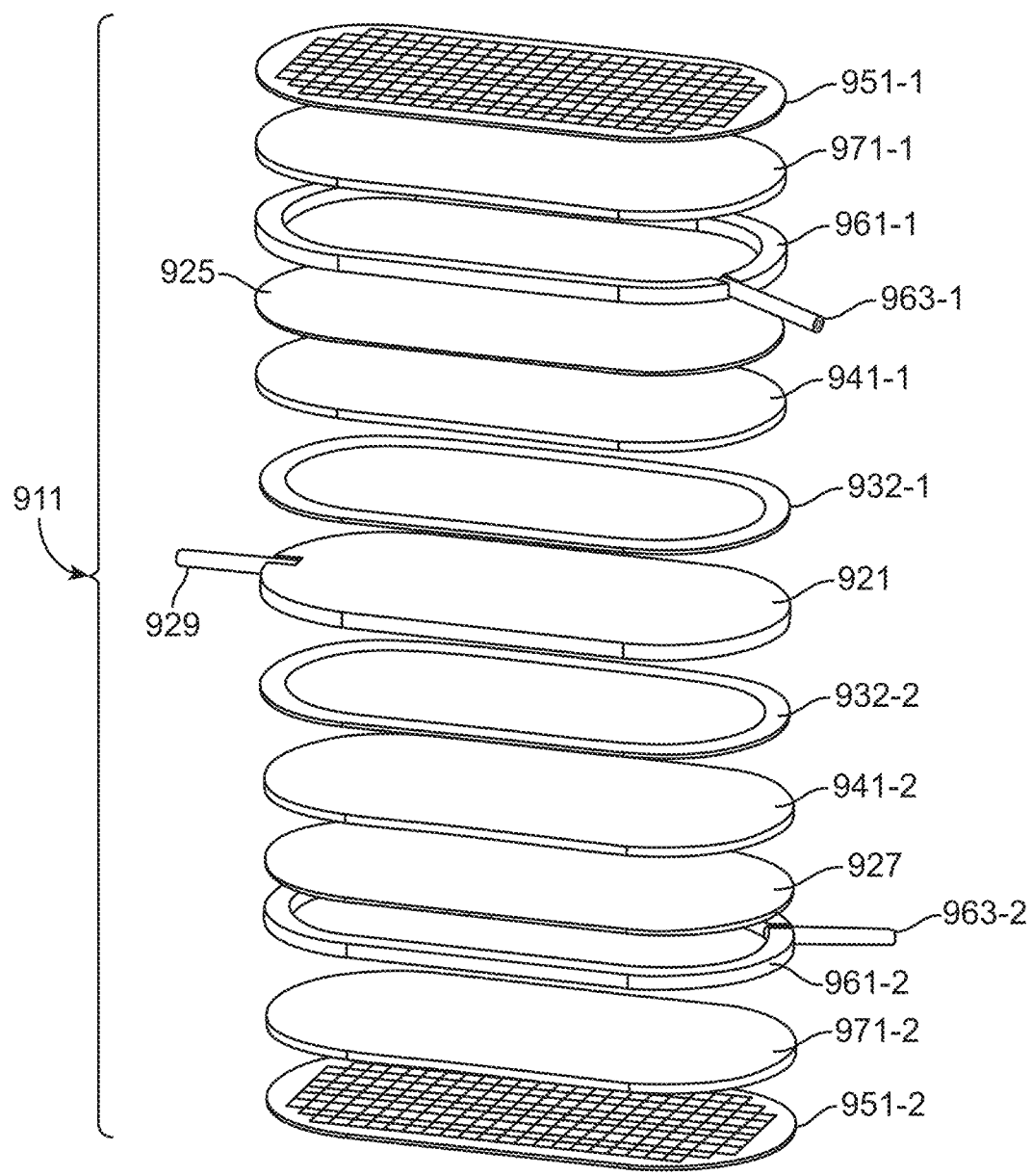
FIG. 10 is a simplified exploded perspective view of a first embodiment of a combined gas diffuser/cell capsule device constructed according to the present invention, the combined gas diffuser/cell capsule device being shown prior to heat-sealing.

Referring now to FIG. 10, there is shown a view of a first embodiment of a combined gas diffuser/cell capsule device constructed according to the present invention, the combined gas diffuser/cell capsule device being represented generally by reference numeral 911. (For simplicity and clarity, certain aspects of combined gas diffuser/cell capsule device 911 that are not critical to an understanding of the present invention are either not shown or described herein or are shown and/or described herein in a simplified manner.)

Combined gas diffuser/cell capsule device 911 may be similar in many respects to gas delivery device 511. For example, combined gas diffuser/cell capsule device 911 may comprise a porous core 921 generally similar to porous core 521, diffusion membranes 925 and 927 generally similar to diffusion membranes 525 and 527, respectively, thermoplastic members 932-1 and 932-2 generally similar to thermoplastic members 532-1 and 532-2, respectively, hydrophobic membranes 941-1 and 941-2 generally similar to hydrophobic membranes 541-1 and 541-2, respectively, tissue integration layers 951-1 and 951-2 generally similar to tissue integration layers 551-1 and 551-2, respectively, and a supply tube 929 generally similar to supply tube 529.

Combined gas diffuser/cell capsule device 911 may differ from gas delivery device 511 in that combined gas diffuser/cell capsule device 911 may further comprise first and second reinforced gaskets 961-1 and 961-2 with integrated tubes 963-1 and 963-2, respectively, and first and second porous membranes 971-1 and 971-2. First gasket 961-1 may be positioned directly on top of diffusion membrane 925, and second gasket 961-2 may be positioned directly under diffusion membrane 927. First porous membrane 971-1 may be positioned directly on top of first gasket 961-1 and directly under tissue integration layer 951-1, and second porous membrane 971-2 may be positioned directly under second gasket 961-2 and directly on top of tissue integration layer 951-2.

In this manner, diffusion membranes 925 and 927 may form the inner boundaries of a pair of cell compartments or capsules, gaskets 961-1 and 961-2 with tubes 963-1 and 963-2, respectively, may allow the introduction of cells to the capsules and may form the side walls of such cell compartments, and porous membranes 971-1 and 971-2 may form the outer boundaries of such cell compartments and may act to protect the encapsulated cells from the host immune system, as well as promoting close vascularization and preventing fibrotic encapsulation of the device. Porous membranes 971-1 and 971-2 may be single layer structures or may be laminate structures in which an inner layer acts to exclude components of the host immune system while the outer layer promotes vascularization. Examples of such laminate structures are disclosed in U.S. Patent Application Publication No. US 2015/0112247 A1, which discloses immunoisolation and vascularizing membrane laminates. Advantages of this design include maximization of the interface between the gas compartment and the cell compartments for efficient gas delivery. In addition, bonding of diffusion membranes 925 and 927 and hydrophobic membranes 941-1 and 941-2, respectively, to porous core 921 prevents intrusion of diffusion membranes 925 and 927 into the spaces of the cell capsules when the subject gas is under pressure. Also, use of reinforced cell compartment walls in gaskets 961-1 and 961-2 provides a volume with uniform height for more uniform delivery of gas to encapsulated cells. Further, use of the subject embodiment to deliver gas increases safety by reducing strain at the device perimeter, thus preventing rupture of the gas compartment, the cell compartment, or both. If having a uniform cell capsule wall height is not required, thermoplastic gaskets could be used in place of gaskets 961-1 and 961-2 to form the cell compartments. In this embodiment, tissue integration layers 951-1 and 951-2 may provide additional structural support and may promote integration with host tissue at the implant site.

Figure 11A:
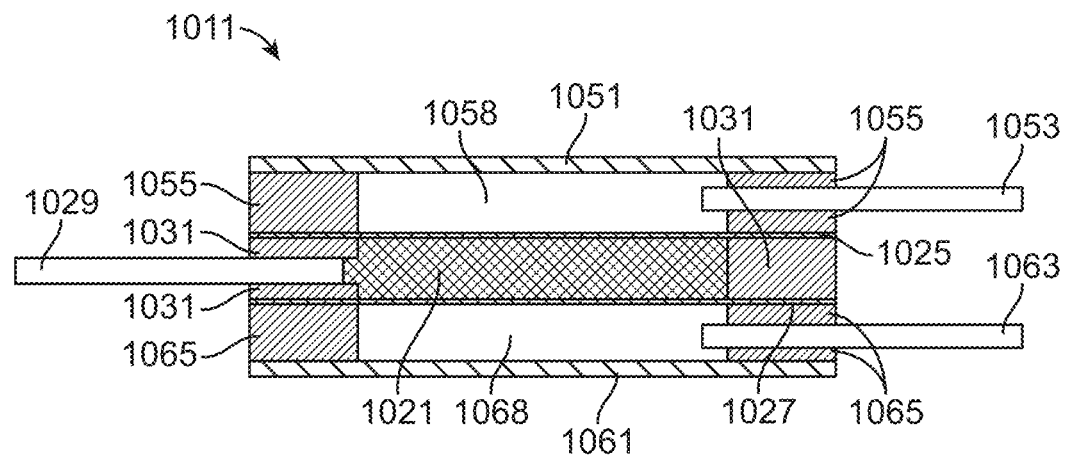
FIG. 11A is a simplified section view of a second embodiment of a combined gas diffuser/cell capsule device constructed according to the present invention.

Referring now to FIG. 11A, there is shown a view of a second embodiment of a combined gas diffuser/cell capsule device constructed according to the present invention, the combined gas diffuser/cell capsule device being represented generally by reference numeral 1011. (For simplicity and clarity, certain aspects of combined gas diffuser/cell capsule device 1011 that are not critical to an understanding of the present invention are either not shown or described herein or are shown and/or described herein in a simplified manner.)

Combined gas diffuser/cell capsule device 1011 may be similar in many respects to gas delivery device 411. For example, combined gas diffuser/cell capsule device 1011 may comprise a porous core 1021 generally similar to porous core 421 that may be made by fusing a pair of porous core layers 1022-1 and 1022-2, diffusion membranes 1025 and 1027 generally similar to diffusion membranes 425 and 427, respectively, a thermoplastic gasket 1031 generally similar to thermoplastic gasket 431 that may be formed by fusing a pair of thermoplastic members 1032-1 and 1032-2, and a supply tube 1029 generally similar to supply tube 429.

Figure 11B:
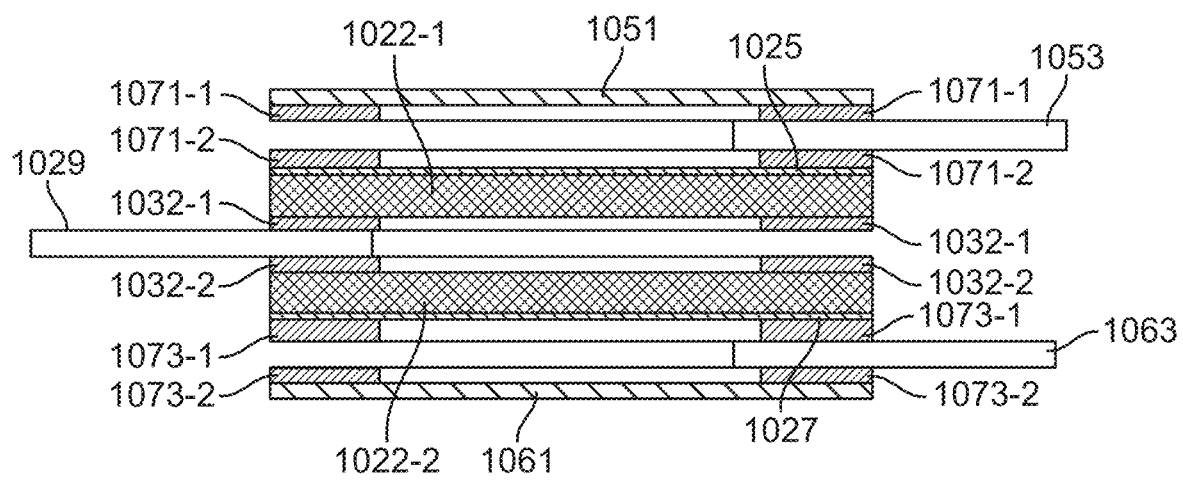
FIG. 11B is a simplified section view of the combined gas diffuser/cell capsule device of FIG. 11A prior to heat-sealing.

Combined gas diffuser/cell capsule device 1011 may differ from gas delivery device 411 in that combined gas diffuser/cell capsule device 1011 may further comprise (i) the combination of a first tissue integration layer 1051, a first cell supply tube 1053, and a first thermoplastic gasket 1055 positioned on top of diffusion membrane 1025 and (ii) the combination of a second tissue integration layer 1061, a second cell supply tube 1063, and a second thermoplastic gasket 1065 positioned under diffusion membrane 1027. In this manner, diffusion membrane 1025, first tissue integration layer 1051, and first thermoplastic gasket 1055 may collectively form a first cell capsule 1058, into which cells may be supplied via first cell supply tube 1053. In addition, diffusion membrane 1027, second tissue integration layer 1061, and second thermoplastic gasket 1065 may collectively form a second cell capsule 1068, into which cells may be supplied via second cell supply tube 1063. After cells have been loaded into the respective cell capsules, cell supply tubes 1053 and 1063 may be sealed shut. As seen best in FIG. 11B, thermoplastic gasket 1031 may be formed by the melting together of thermoplastic members 1032-1 and 1032-2, thermoplastic gasket 1055 may be formed by the melting together of thermoplastic members 1071-1 and 1071-2, and thermoplastic gasket 1065 may be formed by the melting together of thermoplastic members 1073-1 and 1073-2. Porous core layers 1022-1 and 1022-2 may comprise, for example, a non-woven material comprising two different thermoplastics. Diffusion membranes 1025 and 1027 may melt, to some extent, to form a uniform seal at the device perimeter to form a gas-tight seal. Tissue integration layers 1051 and 1061 may promote development of close vascular structures and may minimize development of fibrotic capsules.

As noted above, the gas delivery device of the present invention may be combined with a gas generating device or, alternatively, may be combined with both a gas generating device and one or more cell capsules. For example, according to one embodiment, a system is provided in which both a water electrolyzer and cell compartments are integrated with a gas delivery device. In such a configuration, the oxygen gas delivery may be achieved directly to the cell capsule, having its own vascularized tissue interface on one face, over a very short distance, and hydrogen is allowed to diffuse into the tissue via a vascularized interface at the opposing face. Both interfaces serve as sources of diffused water for supplying the electrolysis reaction which produces the hydrogen and oxygen. The present invention serves as an improvement to existing cell implant systems because, in the present invention, the interfaces between the oxygen gas compartment and the cell capsules, as well as the hydrogen gas compartment and vascularized tissue interface, are significantly better supported against any required pressure differential.

Figure 12:
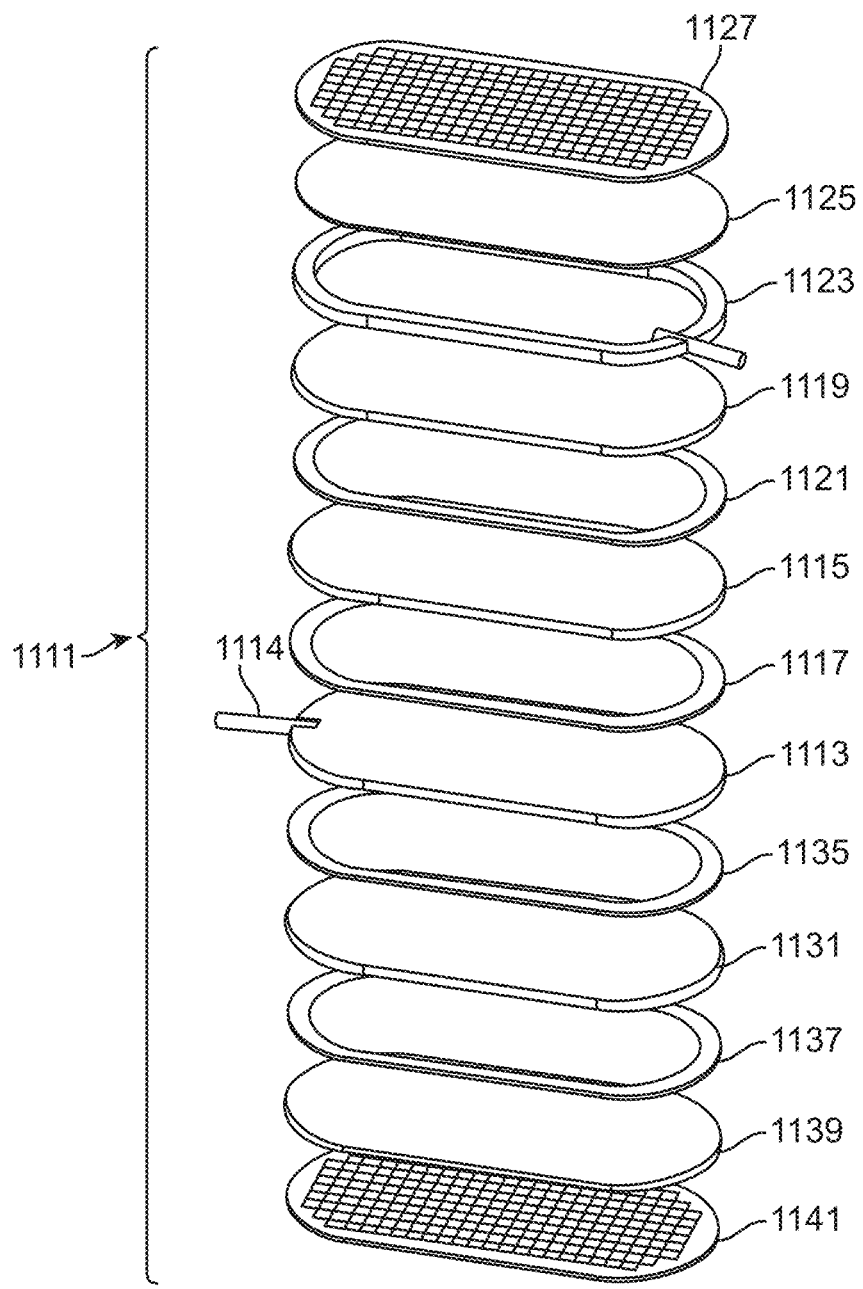
FIG. 12 is a simplified exploded perspective view of a first embodiment of an integrated system constructed according to the present invention and comprising gas generation and gas delivery functionalities, the system being shown prior to heat-sealing.

Referring now to FIG. 12, there is shown a first embodiment of an integrated system constructed according to the present invention and comprising gas generation and gas delivery functionalities, the system being represented generally by reference numeral 1111. (For simplicity and clarity, certain aspects of system 1111 that are not critical to an understanding of the present invention are either not shown or described herein or are shown and/or described herein in a simplified manner.)

System 1111 may comprise a central electrolyzer assembly 1113. Central electrolyzer assembly 1113 may be constructed to utilize water, diffusing in from the local environment or from an internal reservoir, to generate hydrogen and oxygen gases electrochemically. Electrical energy for the electrolysis reaction taking place within central electrolyzer assembly 1113 may be delivered by a power source (not shown) using anodically and cathodically connected wires (not shown) disposed within a tube 1114. Further details of the electrolyzer technology are disclosed in U.S. Patent Application Publication No. US 2015/0112247 A1.

Oxygen thus generated by electrolyzer assembly 1113 may be fed to a first face of a first porous core 1115 that is bonded to electrolyzer assembly 1113 using a first thermoplastic adhesion gasket 1117. An opposing face of first porous core 1115 may be bonded to a first face of first diffusion membrane 1119 using a second thermoplastic adhesion gasket 1121. A gasket 1123 may be positioned directly over the opposite face of first diffusion membrane 1119. An immunoisolation membrane 1125 may be positioned directly over gasket 1123, and a vascularizing membrane 1127 may be positioned directly over immunoisolation membrane 1125. In this manner, first diffusion membrane 1119, gasket 1123, and immunoisolation membrane 1125 may collectively form a cell capsule that may contain therapeutic cells receiving oxygen from electrolyzer assembly 1113. The cells in the capsule are in fluidic communication sufficient for mass transport to and from host tissue to sustain blood sensing, therapeutic response and nutrient delivery, without transfer of immune response agents, via immunoisolation membrane 1125 and vascularizing membrane 1127. The perimeters of the gas diffuser components are sealed using thermoplastic adhesion gaskets 1117 and 1121.

In an analogous fashion, but without intervening cell capsule, electrolytically produced hydrogen may be shunted to the host vasculature via a second porous core 1131 bonded on one face to electrolyzer assembly 1113 with a third thermoplastic adhesion gasket 1135 and bonded on an opposite face using a fourth thermoplastic adhesion gasket 1137 to a second diffusion membrane 1139 and a tissue integration layer 1141. By means of this embodiment, and in variants similar in methods of porous core integration and gas diffusion layer makeup to others claimed herein, it is shown that the integrated electrolyzer, oxygenated cell capsule and hydrogen diffuser device provide a compact cell therapy solution having features amenable to useful rates of gas delivery and safe pressure management.

Figure 13:
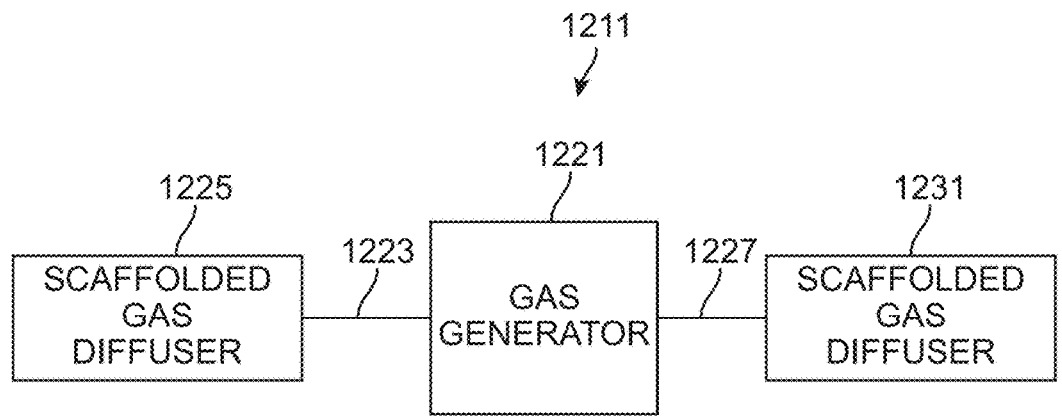
FIG. 13 is a simplified schematic view of a second embodiment of an integrated system constructed according to the present invention and comprising gas generation and gas delivery functionalities.

Referring now to FIG. 13, there is shown a second embodiment of an integrated system constructed according to the present invention and comprising gas generation and gas delivery functionalities, the system being represented generally by reference numeral 1211. (For simplicity and clarity, certain aspects of system 1211 that are not critical to an understanding of the present invention are either not shown or described herein or are shown and/or described herein in a simplified manner.)

System 1211, which may be well-suited for localized or systemic hydrogen therapy, may comprise an implanted gas generator 1221. Gas generator 1221 may be, for example, a water electrolyzer of the type configured to produce oxygen and hydrogen, an example of such a water electrolyzer being disclosed in U.S. Patent Application Publication No. US 2015/0112247 A1. The oxygen produced by gas generator 1221 may be delivered by a tube 1223 to a first implanted scaffolded gas diffuser 1225, which may be a gas delivery device of the type disclosed in the present application. First implanted scaffolded gas diffuser 1225 may be placed in contact with or in close proximity to host tissue to enable facile dissipation of oxygen from scaffolded gas diffuser 1225 to the host tissue. The hydrogen generated by gas generator 1221 may be delivered by a tube 1227 to a second implanted scaffolded gas diffuser 1231, which may be a gas delivery device of the type disclosed in the present application. Second implanted scaffolded gas diffuser 1231 may be placed in contact with or in close proximity to host tissue to enable delivery of hydrogen to the host tissue for local or systemic treatment of disease or injury.

As can readily be appreciated, instead of using system 1211 to administer hydrogen therapeutically and to deliver unwanted oxygen for expulsion from the patient by exhalation, system 1211 may alternatively be used to deliver oxygen to a target tissue for a tissue healing application and to deliver waste hydrogen to a nearby tissue for removal through the circulatory system via exhalation. In such a case, scaffolded gas diffuser 1225 would be placed in contact or in close proximity to the target tissue.

Figure 14:
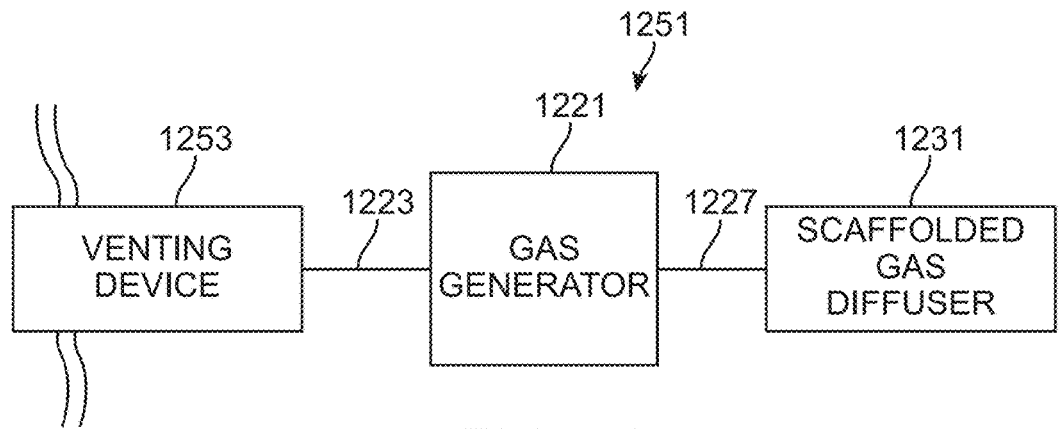
FIG. 14 is a simplified schematic view of a third embodiment of an integrated system constructed according to the present invention and comprising gas generation and gas delivery functionalities.

Referring now to FIG. 14, there is shown a third embodiment of an integrated system constructed according to the present invention and comprising gas generation and gas delivery functionalities, the system being represented generally by reference numeral 1251. (For simplicity and clarity, certain aspects of system 1251 that are not critical to an understanding of the present invention are either not shown or described herein or are shown and/or described herein in a simplified manner.)

System 1251 may be similar in many respects to system 1211, the principal difference between the two systems being that, in system 1251, implanted scaffolded gas diffuser 1225 may be replaced with a percutaneous venting device 1253 for venting of oxygen from the host. Percutaneous venting device may be a device of the type disclosed in U.S. patent application Ser. No. 15/814,298 and may comprise a core layer including a gas-permeable, liquid-impermeable material, an outer layer peripherally surrounding the core layer and including a tissue-integrating material, and an intermediate barrier layer that prevents infiltration of tissue from the outer layer into the core layer and that reduces diffusion of gas from the core layer into the outer layer.

Figure 15:
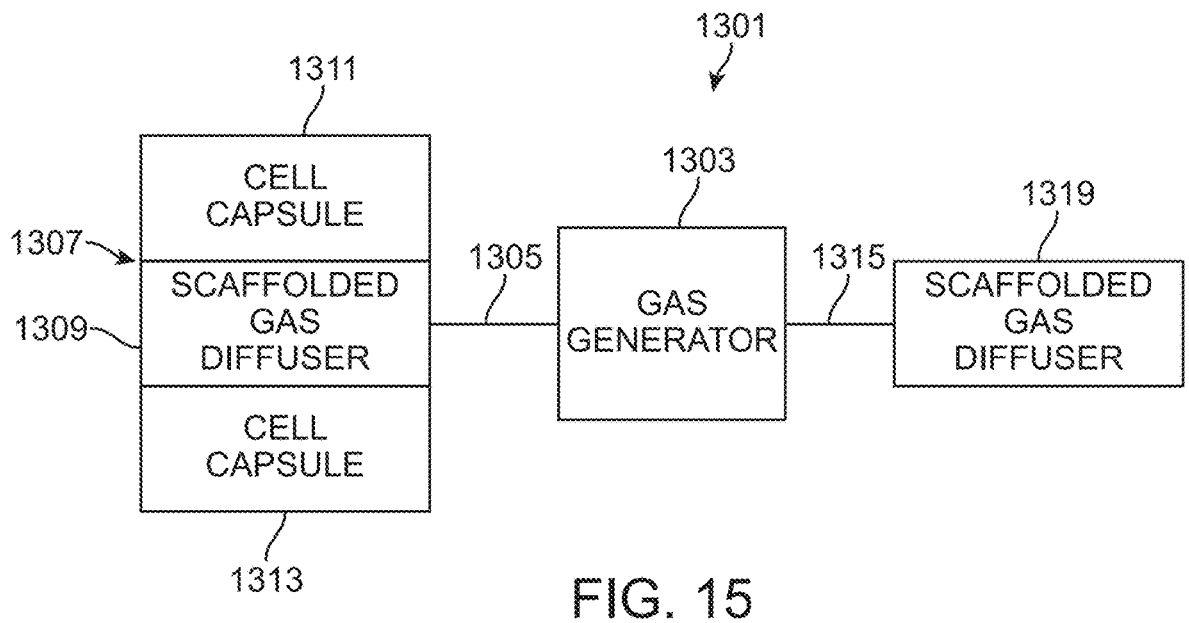
FIG. 15 is a simplified schematic view of a fourth embodiment of an integrated system constructed according to the present invention and comprising gas generation and gas delivery functionalities.

Referring now to FIG. 15, there is shown a fourth embodiment of an integrated system constructed according to the present invention and comprising gas generation and gas delivery functionalities, the system being represented generally by reference numeral 1301. (For simplicity and clarity, certain aspects of system 1301 that are not critical to an understanding of the present invention are either not shown or described herein or are shown and/or described herein in a simplified manner.)

System 1301, which may be used to supply oxygen to a pair of cell capsules, may comprise an implanted gas generator 1303. Gas generator 1303 may be similar to gas generator 1221 and may be a water electrolyzer producing oxygen and hydrogen. Oxygen generated by gas generator 1303 may be delivered by a tube 1305 to an implanted combined gas diffuser/cell capsule 1307. In particular, oxygen may be delivered to a planar scaffolded gas diffuser 1309. Scaffolded gas diffuser 1309 may then deliver the oxygen that it receives to cell capsules 1311 and 1313, which may be coupled to opposing faces of diffuser 1309. The oxygen is preferably generated at a rate sufficient to maintain viability and function of the therapeutic cells. Waste hydrogen generated by gas generator 1303 may be delivered by a tube 1315 to an implanted scaffolded gas diffuser 1319 that enables diffusion of the hydrogen gas through the host tissue and to the circulatory system where it can be removed from the body by exhalation.

Figure 16:
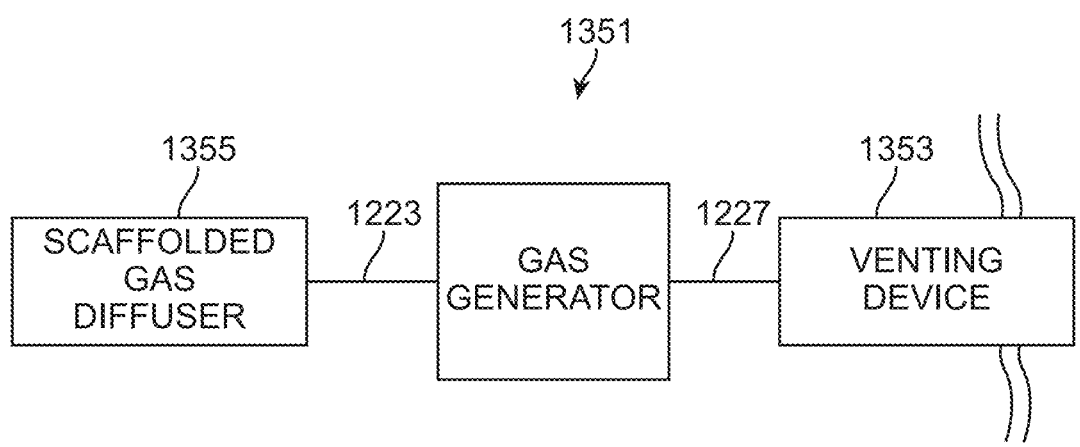
FIG. 16 is a simplified schematic view of a fifth embodiment of an integrated system constructed according to the present invention and comprising gas generation and gas delivery functionalities.

Referring now to FIG. 16, there is shown a fifth embodiment of an integrated system constructed according to the present invention and comprising gas generation and gas delivery functionalities, the system being represented generally by reference numeral 1351. (For simplicity and clarity, certain aspects of system 1351 that are not critical to an understanding of the present invention are either not shown or described herein or are shown and/or described herein in a simplified manner.)

System 1351 may be similar in many respects to system 1251, the principal difference between the two systems being that, in system 1351, hydrogen is conducted by tube 1227 to a percutaneous venting device 1353, which may be similar to percutaneous venting device 1253 of system 1251, and oxygen is conducted by tube 1223 to a scaffolded gas diffuser 1355, which may be positioned in contact with or in close proximity to host tissue for local treatment of disease or injury.

Figure 17A:
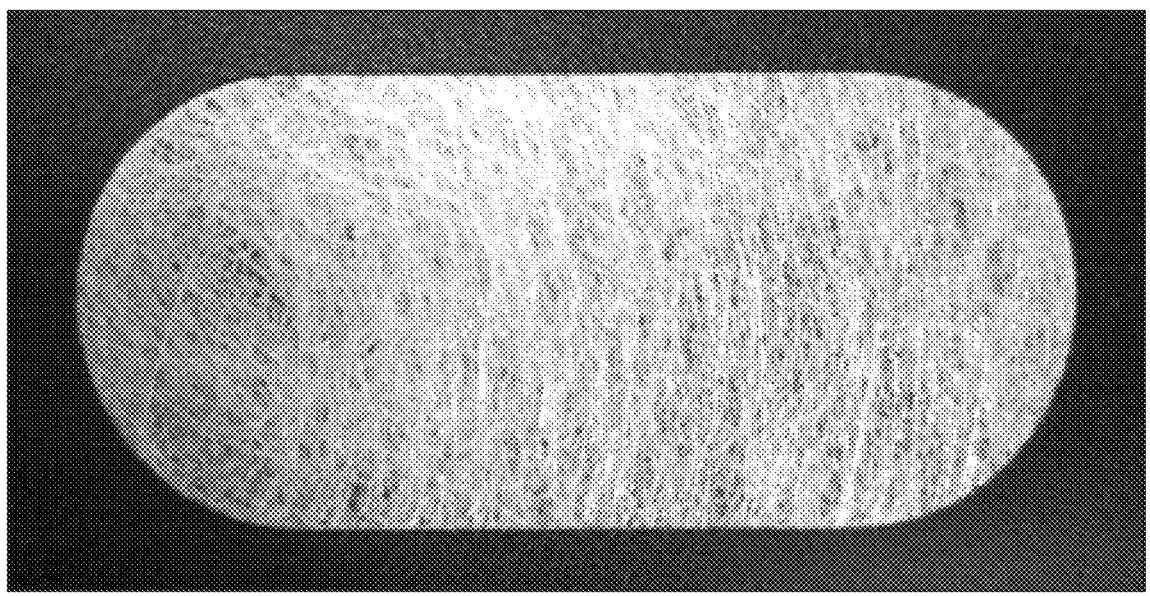
FIGS. 17A and 17B are a photograph and a scanning electron micrograph, respectively, of a spunbonded polyester nonwoven fabric suitable for use as a porous core of a gas delivery device of the present invention.
Figure 17B:
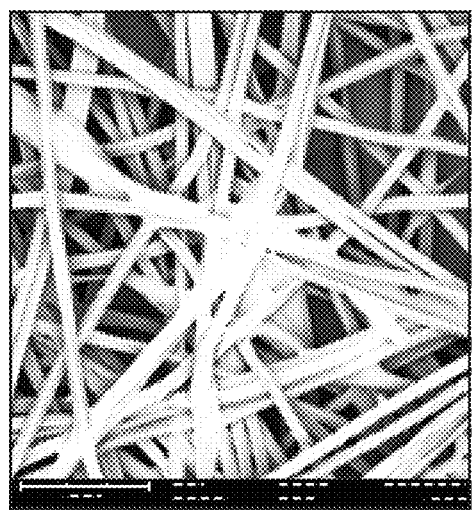
Figure 20:
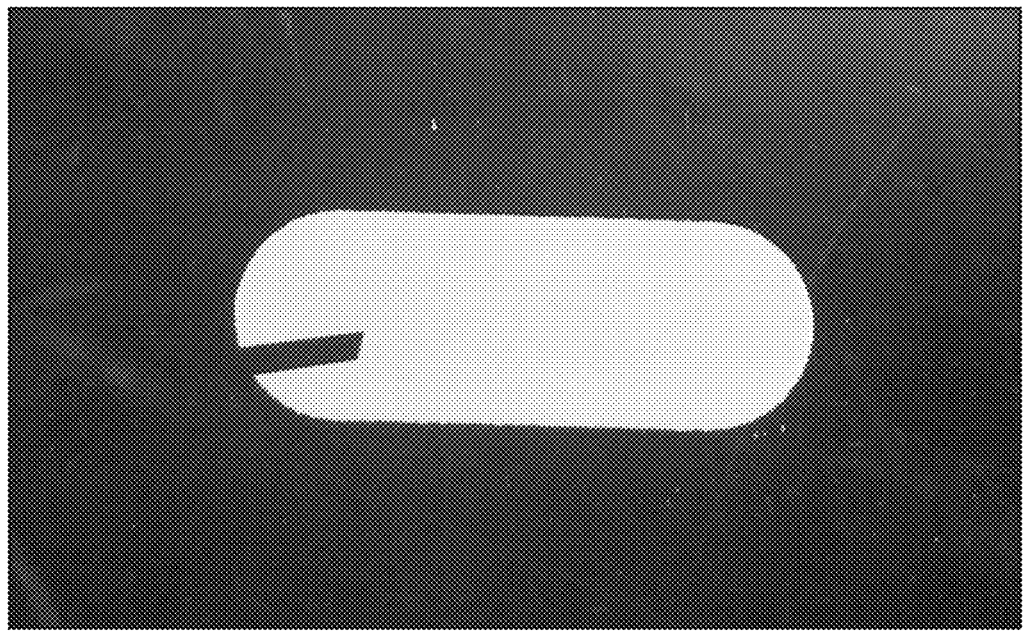
FIG. 20 is a photograph of a sintered, ultra-high molecular weight polyethylene material suitable for use as a porous core of a gas delivery device of the present invention.
Figure 21:
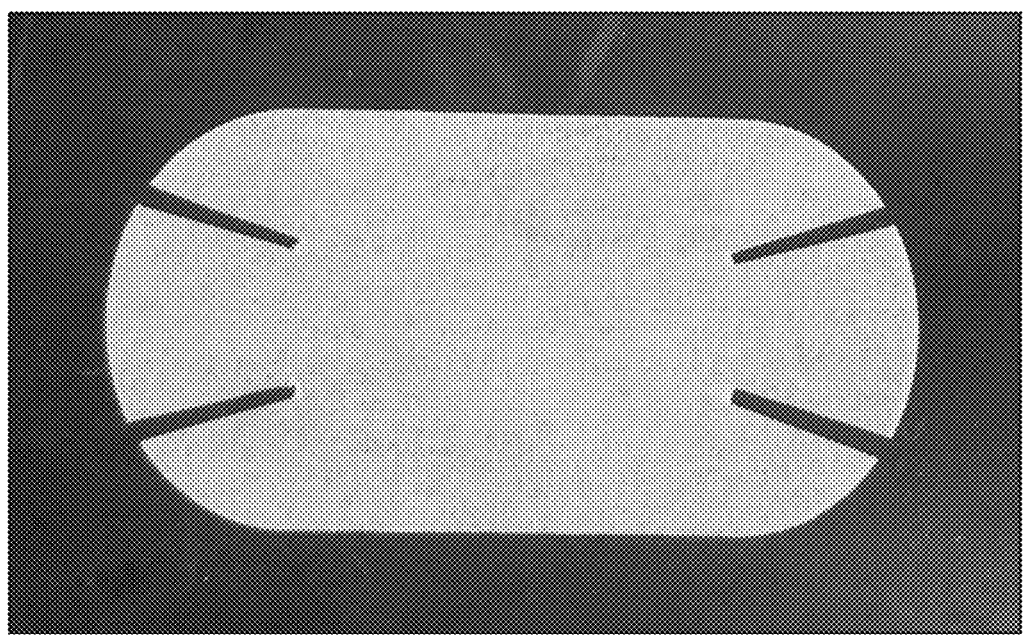
FIG. 21 is a photograph of a non-woven material composed of fibers with a polypropylene core and a low density polyethylene sheath, said non-woven material being suitable for use as a porous core of a gas delivery device of the present invention.

Referring now to FIGS. 17A through 21, there are shown various images of different materials suitable for use as the porous core material of the present invention. More specifically, FIGS. 17A and 17B are a photograph and a scanning electron micrograph, respectively, of a spunbonded polyester nonwoven fabric. FIGS. 18A and 18B are a photograph and a scanning electron micrograph, respectively, of a fabric containing layers of spunbond and meltblown polypropylene. FIG. 19 is a scanning electron micrograph of a porous high density polyethylene film fabricated by flash spinning. FIG. 20 is a photograph of a sintered, ultra-high molecular weight polyethylene material. FIG. 21 is a photograph of a non-woven material composed of fibers with a polypropylene core and a low density polyethylene sheath.

To summarize, the present invention is directed principally at three types of constructions: 1) a scaffolded gas diffuser for delivering gas; 2) a scaffolded gas diffuser with integrated capsules for cellular therapies; and 3) a scaffolded gas diffuser with both an integrated water electrolyzer and integrated cell capsules. The present invention addresses the need to deliver therapeutic gases to tissues or implantable devices inside the body safely and effectively by imparting the scaffolded gas diffuser with a strong, uniform bond between a porous core and outer diffusion membrane(s) which interface with tissue and/or extracellular fluid. The materials used for the porous core and diffusion membrane(s) and the bonding process used to join them are selected so as to result in a unitized structure that substantially resists mechanical expansion under positive internal pressurization, while minimizing the following: occlusion of the open surface area of the diffusion membrane(s); and porosity and surface property losses of all materials in the region of the joined interface.

The following examples are provided for illustrative purposes only and are in no way intended to limit the scope of the present invention:

Example 1

Construction and Testing of a Device of the Design Illustrated in FIG. 4A

Figure 22:
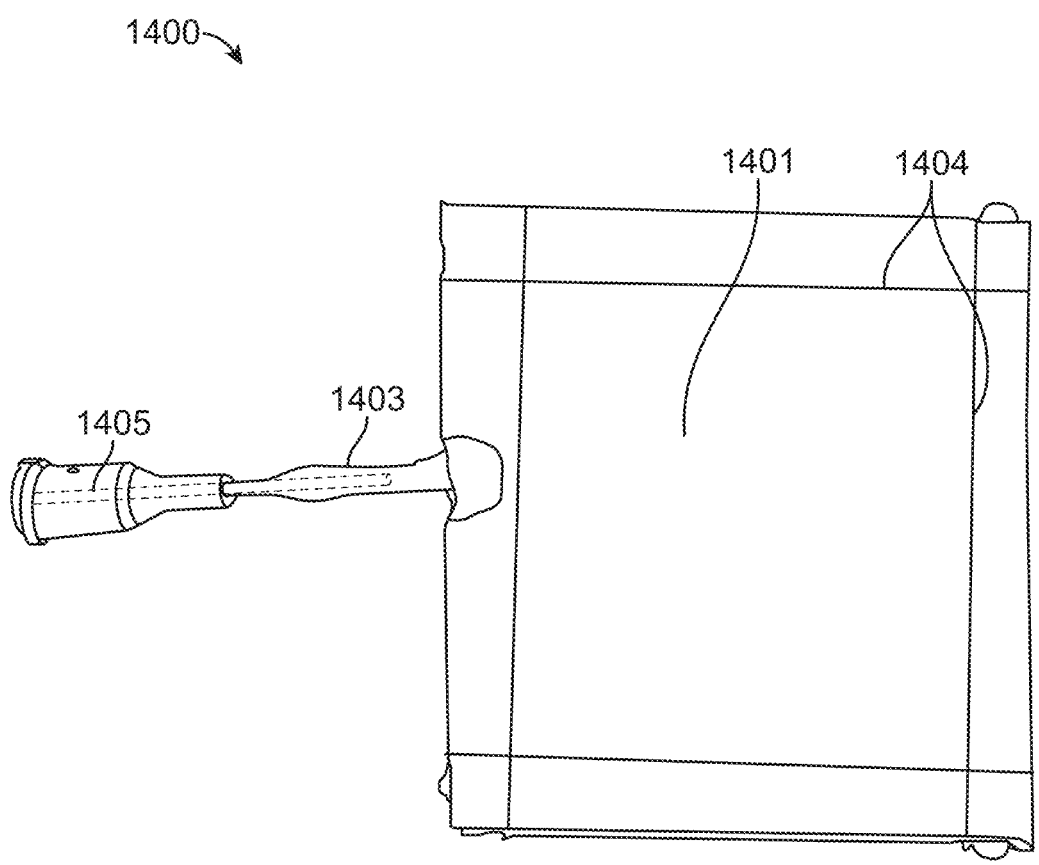
FIG. 22 is a photograph of the gas delivery device of Example 1.

A top-view photograph of a physical embodiment of device 1400 is shown in FIG. 22. The ported scaffolded gas diffuser device was fabricated using a non-woven fabric manufactured from polypropylene core fibers with a sheath of low molecular weight polyethylene (POREX® HRM 36777 non-woven material), hydrophilic ePTFE (BIOPORE® BGCM00010 membrane, MilliporeSigma), and low molecular weight polyethylene tubing with a 1.65 mm outer diameter and a 0.89 mm inner diameter.

The scaffolded gas diffuser portion of the device was prepared by lamination and tested for properties. POREX® HRM 36777 non-woven material and BIOPORE® membrane sheets were cut into squares approximately 2.13 inches per side. A PTFE-coated sheet was placed on the base plate of a heated press (Geo. Knight & Co., Digital Combo). Components were stacked on a PTFE-coated sheet in the following order: BIOPORE® membrane, POREX® HRM 36777 non-woven material, polyethylene tube, POREX® HRM 36777 non-woven material, BIOPORE® membrane. A 0.033" diameter pin gauge was inserted in the tube and extended nearly to the center of the square sheets in order to ensure that a flow path for gas into the device would remain open after all thermal operations. The portion of polyethylene tube that extended away from the sheets of BIOPORE® membrane and POREX® HRM 36777 non-woven material was protected from heat using ⅛" inner diameter silicone tubing. A second PTFE-coated sheet was placed on top of the assembly.

The heated press was set to 255° C., 100 psi (effective pressure was approximately 0.2 psi), and 10 seconds. The press was activated to laminate one side of the device. The PTFE-coated sheets were used to carefully invert the device, and a second round of lamination was performed using the same settings. The scaffolded gas diffuser thus fabricated by these steps, comprising a laminate of porous core (POREX® HRM 36777 non-woven material) and a gas-permeable diffusion membrane (MilliporeSigma BIOPORE® BGCM00010 membrane), had properties suitable for use in the application, as demonstrated by tensile (pull) testing and gas permeation testing.

Pull testing was performed per ASTM D-4541, "Pull-Off Strength of Coatings Using Portable Adhesion Testers", using a P.A.T.T.I. Micro® portable adhesion tester (M.E. Taylor Engineering, Inc., Derwood, Md.) with a low range piston (F1) and Ø1.0" stubs. Laminate samples were attached to an acrylic slab substrate and the tester stubs using 3M™ 467MP adhesive transfer tape. For samples where detachment of the porous core from the diffuser material occurred, or where the porous core was torn apart, the adhesion strength of the laminate is reported in psi. The scaffolded gas diffuser laminate remained adhered up to a tensile stress of 44 psi, where the BIOPORE® material came apart.

Gas permeation testing was performed using a stainless steel filter housing (P/N B-202025, Small Parts, Inc., Miami Lakes, Fla.) and a pressure-indicating mass flow controller (P/N MC-100SCCM-D, Alicat Scientific, Tucson, Ariz.). Laminates were cut out to Ø¾" and clamped into the filter housing. Nitrogen gas was introduced through the filter housing at increasing flows from 1 sccm up to 100 sccm while monitoring the filter inlet pressure. The linear fit to the pressure-flow data was used as a permeability figure of merit (PFOM, psi/sccm/cm$^2$ or psi-min/cm), a higher PFOM indicating a greater restriction to flow. Permeability of the as-prepared laminate was not significantly different from that of unlaminated BIOPORE® film.

The ported device was then fabricated using the scaffolded gas diffuser laminate. The perimeter was sealed using an American International Electric Type AIE-200, 260W impulse sealer. Sufficient heat was applied to melt both the polyethylene and polypropylene components of the POREX® HRM 36777 non-woven material in order to form a uniform perimeter seal. Additional heat was applied locally to the area around the polyethylene tube using a soldering iron. After sealing the effective active surface area for gas diffusion was approximately 4.9 in$^2$.

The gauge pin was removed from the assembly, and a 20 gauge, blunt Luer lock needle 1405 was inserted into the polyethylene tube 1403. Epoxy was used to form a permanent seal between the needle and the tube. Visible in the photograph are the BIOPORE® diffusive membrane surface 1401 and the perimeter seal 1404. The BIOPORE® membrane is not melted under the fabrication conditions. The perimeter seal area is more transparent due to the molten thermoplastic from the porous core penetrating the ePTFE diffusion membrane pores at the perimeter.

Figure 23:
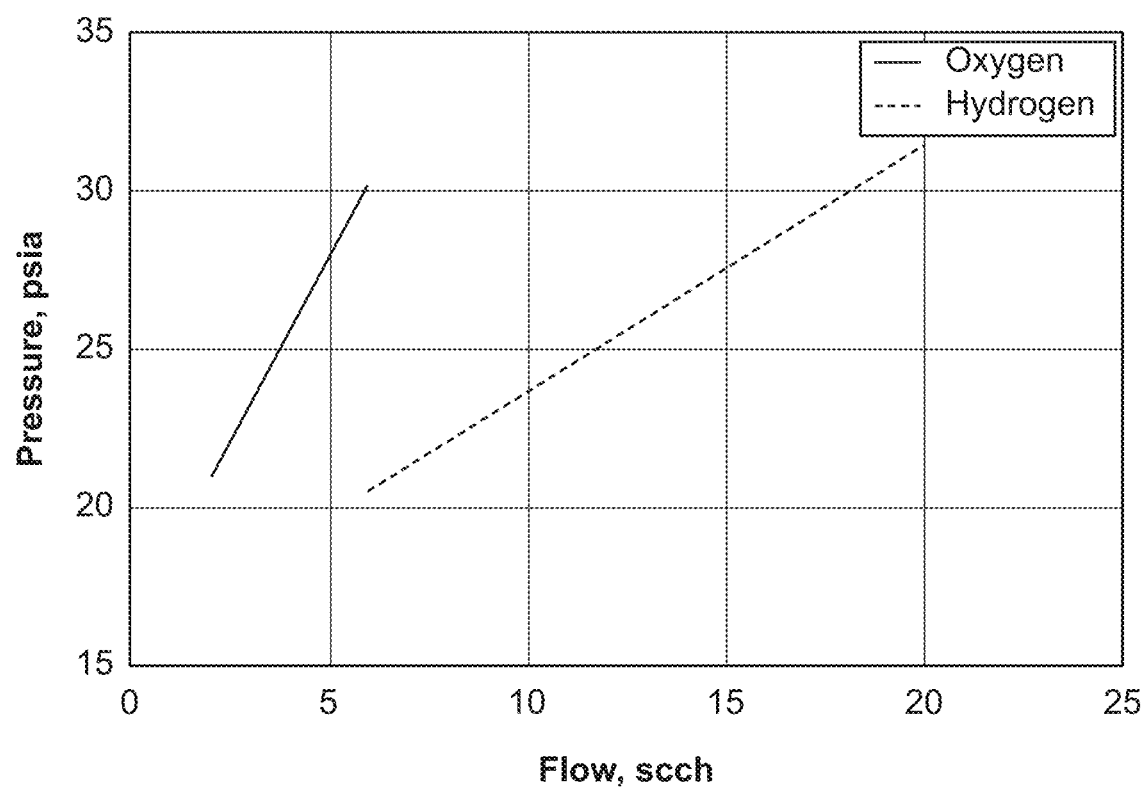
FIG. 23 is a graph depicting the results discussed in Example 1.

The resulting device was wetted in deionized water and was successfully pressure tested to 15 psig. The device was then connected to an electrochemical device to provide gas flow for additional testing. The scaffolded gas diffuser was suspended in a stirred beaker filled with deionized water. The water was sparged with $N_2$ gas to reduce $O_2$ partial pressure and more closely mimic the environment in body tissues. Pressure (psia) was monitored and was plotted against $O_2$ flow rate. The electrochemical device was reconfigured to supply $H_2$ gas to the capsule and the experiment was repeated. The results, shown in FIG. 23, show that an $O_2$ flow of 6 SCCH (standard cubic centimeters per hour) resulted in a pressure in the scaffolded gas diffuser of approximately 30 psia (approximately 15 psi above ambient pressure). A $H_2$ flow of 20 SCCH resulted in a pressure in the diffuser of approximately 32 psia (approximately 17 psi above ambient pressure). The device did not deform significantly under pressure. The device thickness at ambient pressure was 0.78 mm. The thickness increased by 26% when the device was pressurized to 15 psi to 0.90 mm. The increase in thickness was uniform in the non-sealed areas of the diffusion membrane and the device returned to its original thickness upon depressurization thereby demonstrating no permanent deformation. No delamination of the device or materials was observed.

Example 2

Construction and Testing of a Device of the Design Illustrated in FIG. 5A

A scaffolded gas diffuser was fabricated using a non-woven fabric manufactured from polypropylene core fibers with a sheath of low molecular weight polyethylene (POREX® HRM 36777 non-woven material), hydrophilic PVDF (DURAPORE® GVWP00010 membrane, MilliporeSigma), 0.005" thick low density polyethylene sheet, and low molecular weight polyethylene tubing with a 1.09 mm outer diameter and a 0.38 mm inner diameter (Instech BTPE-20).

The scaffolded gas diffuser portion of the device was prepared by lamination and tested for properties. POREX® HRM 36777HRM non-woven material, DURAPORE® GVWP00010 membrane, and polyethylene sheets were cut into squares approximately 1⅛ inches per side. The centers of the resulting polyethylene squares were removed to leave an approximately ⅜" wide gasket.

A 6"×6"×⅛" piece of PTFE was placed on the base plate of the heated press to ease assembly and to increase the actual pressure applied during lamination. A PTFE-coated sheet was placed on the PTFE square. Components were stacked on the PTFE-coated sheet in the following order: DURAPORE® GVWP00010 membrane, POREX® HRM 36777 non-woven material, polyethylene gasket, polyethylene tube, polyethylene gasket, POREX® HRM 36777 non-woven material, DURAPORE® GVWP00010 membrane. A 0.013" diameter pin gauge was inserted in the tube and extended nearly to the center of the square sheets in order to ensure that a flow path for gas into the device would remain open after all thermal operations. The portion of polyethylene tube that extended away from the sheets of DURAPORE® GVWP00010 membrane and POREX® HRM 36777 non-woven material was protected from heat using 1/16" inner diameter silicone tubing. A second PTFE-coated sheet was placed on top of the assembly.

The heated press was set to 255° C., 100 psi (effective pressure was approximately 1.2 psi), and 20 s. The press was activated to laminate one side of the device. The PTFE-coated sheets were used to carefully invert the device and a second round of lamination was performed using the same settings.

The scaffolded gas diffuser thus fabricated by these steps, comprising a laminate of porous core (POREX® HRM 36777 non-woven material) and a gas-permeable diffusion membrane (MilliporeSigma DURAPORE® GVWP00010 membrane), had properties suitable for use in the application, as demonstrated by tensile (pull) testing and gas permeation testing. Pull testing and gas permeation testing were performed as described in Example 1. By pull testing, it was observed that the scaffolded gas diffuser laminate remained adhered up to a tensile stress of 50 psi, where the DURAPORE® material released from the POREX® core. Permeability of the as-prepared laminate was not significantly different from that of unlaminated DURAPORE® film.

Figure 24:
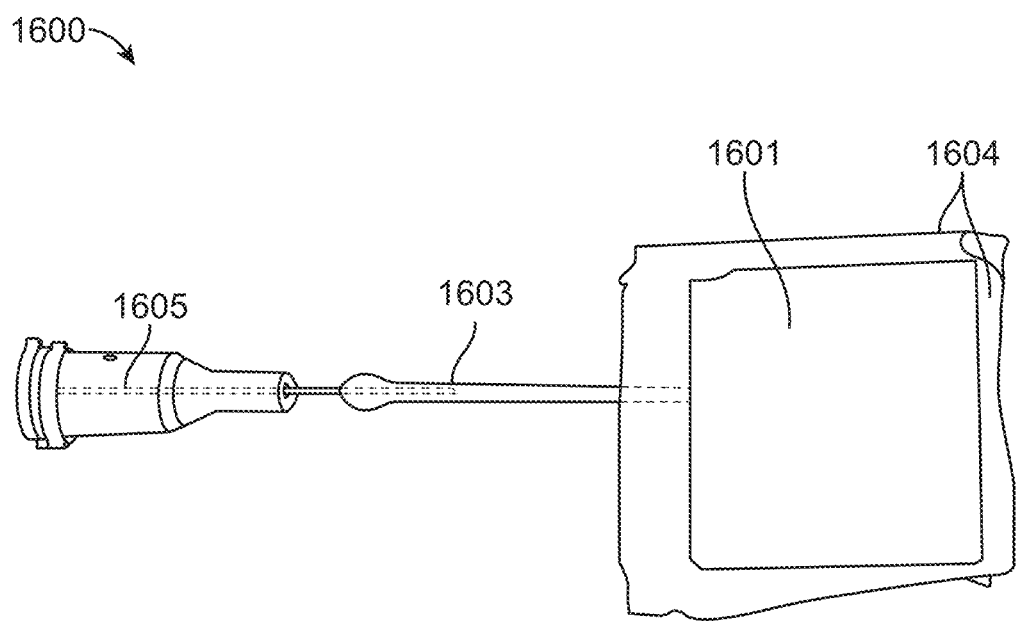
FIG. 24 is a photograph of the gas delivery device of Example 2.

The ported device was then fabricated using the scaffolded gas diffuser laminate. A photograph of the resulting device 1600 is depicted in FIG. 24. The perimeter was sealed using an American International Electric Type AIE-200, 260W impulse sealer. Sufficient heat was applied to melt the polyethylene and polypropylene components of the POREX® HRM 36777 non-woven material, as well as the DURAPORE® GVWP00010 membrane, to form a uniform perimeter seal 1604. Additional heat was applied locally to the area around the polyethylene tube using a soldering iron. After sealing, the effective active surface area for gas diffusion was approximately 1.3 in². The area of the perimeter seal is transparent relative to the white surface of the DURAPORE® GVWP00010 membrane 1601, indicating that all of the polymers including the polyethylene and polypropylene of the porous core, and the PVDF of the DURAPORE® GVWP00010 membrane melted during sealing to form a uniform bond. This configuration is particularly preferred since the materials are permanently bonded to each other as compared with the device in FIG. 22, in which the porous core material melts and seeps into the pores in the ePTFE membrane to form a less strong bond by mechanical interference.

The gauge pin was removed from the assembly and a 25 gauge, blunt Luer lock needle 1605 was inserted into the polyethylene tube 1603. Epoxy was used to form a permanent seal between the needle and the tube. The device was wetted in deionized water and was pressurized to approximately 15 psig without delamination. The device thickness at ambient pressure was 1.03 mm. The thickness increased by 35% when the device was pressurized to 15 psi to 1.39 mm. The increase in thickness was uniform in the non-sealed areas of the diffusion membrane and the device returned to its original thickness upon depressurization thereby demonstrating no permanent deformation. No delamination of the device or materials was observed.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. An implantable gas delivery device, the implantable gas delivery device comprising:
   (a) a porous core, the porous core having an open volume and permitting transport of gas throughout the open volume, the porous core having a tensile strength in all directions sufficient to withstand a tensile stress without permanent deformation, wherein the porous core is shaped to comprise two opposing surfaces and a periphery, the periphery disposed between the two opposing surfaces;
   (b) at least one gas-permeable diffusion membrane, the at least one gas-permeable diffusion membrane comprising a first gas-permeable diffusion membrane and a second gas-permeable diffusion membrane, the first gas-permeable diffusion membrane being fixedly coupled to one of the two opposing surfaces of the porous core, the second gas-permeable diffusion membrane being fixedly coupled to another of the two opposing surfaces of the porous core, whereby deformation and/or delamination of the at least one gas-permeable diffusion membrane is limited by attachment of the at least one gas-permeable diffusion membrane to the porous core;
   (c) a gas supply tube, the gas supply tube having a first end inserted through the periphery of the porous core and into the porous core at a position along the periphery of the porous core that is located between the first gas-permeable diffusion membrane and the second gas-permeable diffusion membrane, the gas supply tube having a second end adapted to receive gas from a gas source;
   (d) wherein any surfaces of the porous core unoccupied by the at least one gas-permeable diffusion membrane and the gas supply tube are sealed gas-tight; and
   (e) wherein the implantable gas delivery device has a planar geometry and a gas-tight seal and, when pressurized, maintains the planar geometry and the gas-tight seal.

2. The implantable gas delivery device of claim 1 wherein the porous core comprises a biocompatible material selected from the group consisting of one or more of sintered polymers, woven and non-woven polymers, rigid open cell foams, porous ceramics, porous metals, and combinations thereof.

3. The implantable gas delivery device of claim 2 wherein the sintered polymers are selected from the group consisting of sintered polyethylene, sintered polypropylene, sintered polyethylene terephthalate, sintered polyvinylidene fluoride, sintered polytetrafluoroethylene, and combinations thereof.

4. The implantable gas delivery device of claim 2 wherein the woven and non-woven polymers comprise a woven or non-woven polymer mesh, the woven or non-woven polymer mesh comprising a material selected from the group consisting of polyethylene terephthalate, polyethylene, polypropylene, polyamide, polyvinylidene fluoride, and combinations thereof.

5. The implantable gas delivery device of claim 1 wherein the porous core is a monolithic structure made of a single layer.

6. The implantable gas delivery device of claim 1 wherein the porous core is a composite structure made of a plurality of layers and/or a plurality of materials.

7. The implantable gas delivery device of claim 1 wherein the porous core is formed by fusing together two layers.

8. The implantable gas delivery device of claim 1 wherein the at least one gas-permeable diffusion membrane comprises a porous membrane.

9. The implantable gas delivery device of claim 8 wherein the porous membrane comprises a hydrophilic microporous membrane.

10. The implantable gas delivery device of claim 9 wherein the hydrophilic microporous membrane is selected from the group consisting of microporous hydrophilized expanded polytetrafluoroethylene membranes, microporous hydrophilic polyvinylidene fluoride membranes, microporous polyethersulfone membranes, hydrophilized microporous polyethylene terephthalate track etch membranes, microporous hydrophilic polyethylene membranes, and combinations thereof.

11. The implantable gas delivery device of claim 1 wherein the at least one gas-permeable diffusion membrane comprises a non-porous, gas-permeable material.

12. The implantable gas delivery device of claim 11 wherein the non-porous, gas-permeable material comprises a silicone layer.

13. The implantable gas delivery device of claim 1 wherein the at least one gas-permeable diffusion membrane is a monolithic structure made of a single layer.

14. The implantable gas delivery device of claim 1 wherein the at least one gas-permeable diffusion membrane is a laminate structure comprising a plurality of layers.

15. The implantable gas delivery device of claim 14 wherein the laminate structure comprises a hydrophilic microporous membrane and a hydrophobic membrane, the hydrophobic membrane facing towards the porous core, the hydrophilic membrane facing away from the porous core.

16. The implantable gas delivery device of claim 14 wherein the laminate structure comprises a hydrophilic microporous membrane and a vascularizing membrane, the hydrophilic microporous membrane facing towards the porous core, the vascularizing membrane facing away from the porous core.

17. The implantable gas delivery device of claim 1 wherein the at least one gas-permeable diffusion membrane is directly bonded to the porous core.

18. The implantable gas delivery device of claim 1 wherein the at least one gas-permeable diffusion membrane is indirectly bonded to the porous core.

19. The implantable gas delivery device of claim 1 wherein the periphery extends between the two opposing surfaces.

20. The implantable gas delivery device of claim 1 wherein the porous core is sealed gas-tight by an integral edge-seal of the porous core.

21. The implantable gas delivery device of claim 1 wherein the porous core is sealed gas-tight by edge-sealing together the first and second gas-permeable diffusion membranes or by compressing and melting the porous core around its edges so that the compressed and melted porous core flows into the first and second gas-permeable membranes to form a seal or by compressing and melting together the porous core and the first and second gas-permeable membranes around their respective edges.

22. The implantable gas delivery device of claim 1 wherein the porous core is sealed gas-tight with a gasket.

23. The implantable gas delivery device of claim 22 wherein the gasket is a structural gasket.

24. The implantable gas delivery device of claim 22 wherein the gasket is a thermoplastic gasket.

25. The implantable gas delivery device of claim 1 further comprising at least one tissue-integrating layer, the at least one tissue-integrating layer being coupled to the at least one gas-permeable diffusion membrane on a side opposite to the porous core.

26. The implantable gas delivery device of claim 1 further comprising at least one hydrophobic layer, the at least one hydrophobic layer being interposed between the at least one gas-permeable diffusion membrane and the porous core.

27. An implant device, the implant device comprising:
(a) the implantable gas delivery device of claim 1; and
(b) at least one capsule containing implanted cells or tissues, the at least one capsule being in direct contact with the implantable gas delivery device to receive gas therefrom.

28. The implant device of claim 27 wherein the at least one capsule comprises a plurality of capsules containing implanted cells or tissues, each of the plurality of capsules being in direct contact with the implantable gas delivery device to receive gas therefrom.

29. An implant system, the implant system comprising:
(a) an implantable gas source, the implantable gas source comprising a first outlet for outputting a first gas;
(b) the implantable gas delivery device of claim 1, wherein the gas supply tube of the implantable gas delivery device is fluidically coupled to the first outlet of the implantable gas source so as to receive the first gas from the implantable gas source.

30. The implant system of claim 29 wherein the implantable gas source is a water electrolyzer.

31. The implant system of claim 30, wherein the implantable gas source further has a second outlet for outputting a second gas, the implant system further comprising a percutaneous venting device, the percutaneous venting device being fluidically coupled to the second outlet of the implantable gas source so as to receive the second gas from the implantable gas source.

32. The implant system of claim 31 wherein the first gas received by the implantable gas delivery device is oxygen and wherein the second gas received by the percutaneous venting device is hydrogen.

33. The implant system of claim 31 wherein the first gas received by the implantable gas delivery device is hydrogen and wherein the second gas received by the percutaneous venting device is oxygen.

34. An implant system, the implant system comprising:
(a) an implantable gas source, the implantable gas source comprising a first outlet for outputting a first gas and a second outlet for outputting a second gas;
(b) first and second implantable gas delivery devices, each of the first and second implantable gas delivery devices being identical to the implantable gas delivery device of claim 1, wherein the gas supply tube of the first implantable gas delivery device is fluidically coupled to the first outlet of the implantable gas source so as to receive the first gas from the implantable gas source and wherein the gas supply tube of the second implantable gas delivery device is fluidically coupled to the second outlet of the implantable gas source so as to receive the second gas from the implantable gas source.

35. The implant system as claimed in claim 34 further comprising at least one capsule containing cells and/or tissues, the at least one capsule being in direct contact with the first implantable gas delivery device to receive the first gas therefrom.

36. A method of delivering a therapeutic gas to a patient, the method comprising the steps of:
(a) providing the implantable gas delivery device of claim 1;

(b) implanting the implantable gas delivery device in an aqueous environment in a patient at a location where the at least one gas-permeable diffusion membrane is sufficiently close to tissue that the therapeutic gas released from the at least one gas-permeable diffusion membrane is take up by the circulatory system of the patient as the therapeutic gas is dissolved in an aqueous medium; and (c) supplying the therapeutic gas to the implantable gas delivery device, whereby the therapeutic gas is released from the at least one gas-permeable diffusion membrane as the therapeutic gas is dissolved in the aqueous medium.

37. The method as claimed in claim 36 wherein the therapeutic gas is hydrogen.

38. An implant device comprising:
a central electrolyzer assembly, the central electrolyzer assembly having a first face outputting oxygen and a second face outputting hydrogen;
a first porous core fluidically and mechanically coupled to the first face of the central electrolyzer assembly, the first porous core having an open volume and permitting transport of gas throughout the open volume, the first porous core having a tensile strength in all directions sufficient to withstand a tensile stress without permanent deformation;
a second porous core fluidically and mechanically coupled to the second face of the central electrolyzer assembly, the second porous core having an open volume and permitting transport of gas throughout the open volume, the second porous core having a tensile strength in all directions sufficient to withstand a tensile stress without permanent deformation; and
a cell capsule, the cell capsule including a first gas-permeable diffusion membrane, the first gas-permeable diffusion membrane being fixedly coupled to a surface of the first porous core opposite the central electrolyzer assembly, whereby deformation and/or delamination of the first gas-permeable diffusion membrane is limited by attachment of the first gas-permeable diffusion membrane to the first porous core.

39. An implantable gas delivery device, the implantable gas delivery device comprising:
(a) a porous core, the porous core having an open volume and permitting transport of gas throughout the open volume, the porous core having a tensile strength in all directions sufficient to withstand a tensile stress without permanent deformation, wherein the porous core has a top, a bottom, and an end, the end disposed between the top and the bottom;
(b) at least one gas-permeable diffusion membrane, the at least one gas-permeable diffusion membrane comprising a first gas-permeable diffusion membrane and a second gas-permeable diffusion membrane, the first gas-permeable diffusion membrane being positioned over the porous core and fixedly coupled to the top of the porous core, the second gas-permeable diffusion membrane being positioned below the porous core and fixedly coupled to the bottom of the porous core, whereby deformation and/or delamination of the at least one gas-permeable diffusion membrane is limited by attachment of the at least one gas-permeable diffusion membrane to the porous core;
(c) a gas supply tube, the gas supply tube having a first end inserted through the end of the porous core and into the porous core at a position that is located below the top of the porous core and above the bottom of the porous core, the gas supply tube having a second end adapted to receive gas from a gas source;
(d) wherein any surfaces of the porous core unoccupied by the at least one gas-permeable diffusion membrane and the gas supply tube are sealed gas-tight; and
(e) wherein the implantable gas delivery device has a geometry and a gas-tight seal and, when pressurized, maintains the geometry and the gas-tight seal.

* * * * *